United States Patent
Bara et al.

(10) Patent No.: US 11,912,825 B2
(45) Date of Patent: Feb. 27, 2024

(54) POLYMERS DERIVED FROM 2,2'-BISIMIDAZOLES

(71) Applicant: The Board of Trustees of The University of Alabama, Tuscaloosa, AL (US)

(72) Inventors: Jason E. Bara, Tuscaloosa, AL (US); Kathryn E. O'Harra, Tuscaloosa, AL (US); Irshad Kammakakam, Tuscaloosa, AL (US)

(73) Assignee: The Board of Trustees of The University of Alabama, Tuscaloosa, AL (US)

( * ) Notice: Subject to any disclaimer, the term of this patent is extended or adjusted under 35 U.S.C. 154(b) by 176 days.

(21) Appl. No.: 17/154,451

(22) Filed: Jan. 21, 2021

(65) Prior Publication Data

US 2021/0301085 A1 Sep. 30, 2021

Related U.S. Application Data

(60) Provisional application No. 62/994,608, filed on Mar. 25, 2020.

(51) Int. Cl.
| | |
|---|---|
| *C08G 73/18* | (2006.01) |
| *C08G 73/06* | (2006.01) |
| *C07D 235/20* | (2006.01) |
| *C08L 79/04* | (2006.01) |
| *C08G 73/10* | (2006.01) |

(52) U.S. Cl.
CPC ....... *C08G 73/0616* (2013.01); *C07D 235/20* (2013.01); *C08G 73/1039* (2013.01); *C08G 73/18* (2013.01); *C08L 79/04* (2013.01); *C08G 73/1085* (2013.01); *C08L 2205/025* (2013.01); *C08L 2205/035* (2013.01)

(58) Field of Classification Search
None
See application file for complete search history.

(56) References Cited

U.S. PATENT DOCUMENTS

2009/0131623 A1* 5/2009 Hay .................. C08G 65/4031
528/172

OTHER PUBLICATIONS

Shang, Soluble N-Substituted Poly(Benzimidazole imide)s via C—N Coupling Reaction; Polymer International 65 (2016) pp. 332-338. (Year: 2016).*
Hawley's Condensed Chemical Dictionary (2016) p. 45. (Year: 2016).*
He, Synthesis and Characterization of Series Monomers and Polymers of 2,2' Biimidazole ; Polymer Preprints (2001) 42(2) pp. 380-381. (Year: 2001).*
Wasserscheid, Peter, and Wilhelm Keim. "Ionic liquids—new "solutions" for transition metal catalysis." Angewandte Chemie International Edition 39.21 (2000): 3772-3789.
Welton, Thomas. "Room-temperature ionic liquids. Solvents for synthesis and catalysis." Chemical reviews 99.8 (1999): 2071-2084.
R. T. Carlin and J. S. Wilkes, in Chemistry of Nonaqueous Solutions, Current Progress, G. Mamantov and A. I. Popov, Eds., pp. 277, VCH Publisher, New York, (1994).

* cited by examiner

*Primary Examiner* — David J Buttner
(74) *Attorney, Agent, or Firm* — Meunier Carlin & Curfman LLC

(57) ABSTRACT

Disclosed are compositions derived from 2,2'bisimidazoles building blocks and methods of making the same. The disclosed compositions are capable of withstanding temperatures up to 600° C. and substantially flame resistant.

13 Claims, No Drawings

POLYMERS DERIVED FROM 2,2'-BISIMIDAZOLES

CROSS-REFERENCE TO RELATED APPLICATIONS

This application claims the benefit of U.S. Provisional Application No. 62/994,608, filed Mar. 25, 2020, the content of which is incorporated herein by reference in its entirety.

STATEMENT ACKNOWLEDGING GOVERNMENT SUPPORT

This invention was made with government support under Grant No. DE-SC0018181 awarded by the U.S. Department of Energy. The government has certain rights in the invention.

TECHNICAL FIELD

The current disclosure relates to polymers derived from 2,2'-bisimidazoles and methods of making the same.

BACKGROUND

Modern life became dependable on the use of polymers for various applications. The versatility of polymeric materials allows tailoring them almost to any possible application. Advances in polymer chemistry and technology have enabled the development of high-performance polymeric materials such as polybenzimidazoles (PBIs) over the last few decades.

Polybenzimidazoles (PBIs) are well known for their outstanding thermal stability. These polymers have a very high glass transition temperature of about 425° C., no melting point, and decompose at temperatures above >500° C. These polymers are also known for their outstanding heat stability, wear resistance, and chemical resistance.

However, the derivatives of polybenzimidazoles are limited. Also, the manufacturing of polybenzimidazoles and their derivatives is very difficult and expensive.

Thus, there is a need for polymers that have outstanding thermal, chemical- and wear-resistant properties but can also be used to manufacture a large variety of derivatives and can be produced by a simplified manufacturing process. These needs and other needs are at least partially satisfied by the present disclosure.

SUMMARY

In accordance with the purposes of the disclosed materials and methods, as embodied and broadly described herein, the disclosed subject matter, in one aspect, relates to compounds, compositions and methods of making and using compounds and compositions.

In some aspects, disclosed herein is a polymer composition comprising a repeating unit of formula (I):

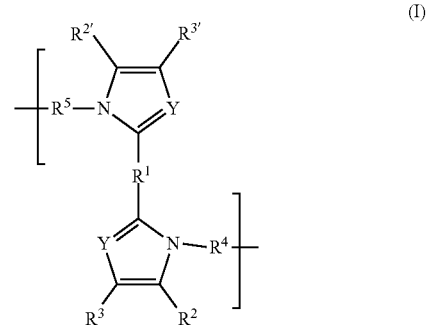

wherein, $R^1$ is selected from null, $C_1$-$C_{10}$ alkyl, $C_1$-$C_{10}$ perfluoroalkyl, $C_6$-$C_{14}$ aryl, or $C_1$-$C_{13}$ heteroaryl;

$R^2$, $R^{2'}$, $R^3$, and $R^{3'}$ are, each independent of the other, selected from hydrogen, $C_1$-$C_{10}$ alkyl, $C_1$-$C_{10}$ alkoxy, $C_6$-$C_{14}$ aryl, $C_1$-$C_{13}$ heteroaryl, $C_6$-$C_{14}$ aryloxy, wherein each of $R^2$, $R^{2'}$, $R^3$, or $R^{3'}$ independent of the other, is optionally substituted with $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, C1-C13 heteroaryl, amino, carbonyl, ester, ether, halide, carboxyl, hydroxy, nitro, cyano, silyl, sulfo-oxo, sulfonyl, sulfone, sulfoxide, thiol, or phosphonyl; or wherein $R^2$ and $R^3$ together form a 6 membered ring containing 6 carbon atoms; and/or wherein $R^{2'}$ and $R^{3'}$ together form a 6 membered ring containing 6 carbon atoms; and wherein $R^2$ and $R^{2'}$ are the same or different; wherein $R^3$ and $R^{3'}$ are the same or different;

$R^4$ and $R^5$ are, independently, $[R^A—R^B—R^C]_m$, wherein:

$R^A$, $R^B$, and $R^C$, each independent of the other, selected from null, carboxyl group, hydroxy group, $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, $C_6$-$C_{14}$ aryloxy, $C_3$-$C_{10}$ cycloalkyl, or $C_3$-$C_{10}$ cycloalkenyl, heterocycloalkyl, imide, cyclic imide, imidazole, polyester, polysulfone, poly(aryl ether ketone), and wherein $R^A$, $R^B$, and $R^C$, are each independently of each other optionally substituted with $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, carbonyl, ester, ether, halide, carboxyl, hydroxy, nitro, cyano, silyl, sulfo-oxo, sulfonyl, sulfone, sulfoxide, thiol, or phosphonyl; wherein any of $R^A$, $R^B$, or $R^C$ are the same or different; wherein at least one of $R^A$, $R^B$, and $R^C$ is not null; wherein m is an integer from 1 to 100; and Y is N or $N^+$—$R^6$, wherein:

$R^6$ is selected from hydrogen, $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, or $C_6$-$C_{14}$ aryloxy, wherein $R^6$ is optionally substituted with $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, imide, cyclic imide, imidazole, imidazolium cation, carbonyl, ester, ether, halide, carboxyl, hydroxy, nitro, cyano, silyl, sulfo-oxo, sulfonyl, sulfone, sulfoxide, thiol, or phosphonyl.

Still, in further aspects, disclosed herein is the polymer composition where Y is $N^+$—$R^6$, the composition further comprises a counter anion X, wherein X is selected from chloride, bromide, iodide, nitrate, dicyanamide, acetate, bis(trifluoromethane)sulfonimide, hexafluorophosphate, tetrafluoroborate, sulfate, phosphate, tris(perfluoroalkyl)trifluorophosphatemesylate, thiocyanide, mesylate, triflate, or tosylate. In still further aspects, also disclosed herein are polymer compositions where when Y is $N^+$—$R^6$, the composition can further comprise an ionic liquid.

In still further aspects, the compositions disclosed herein can comprise:

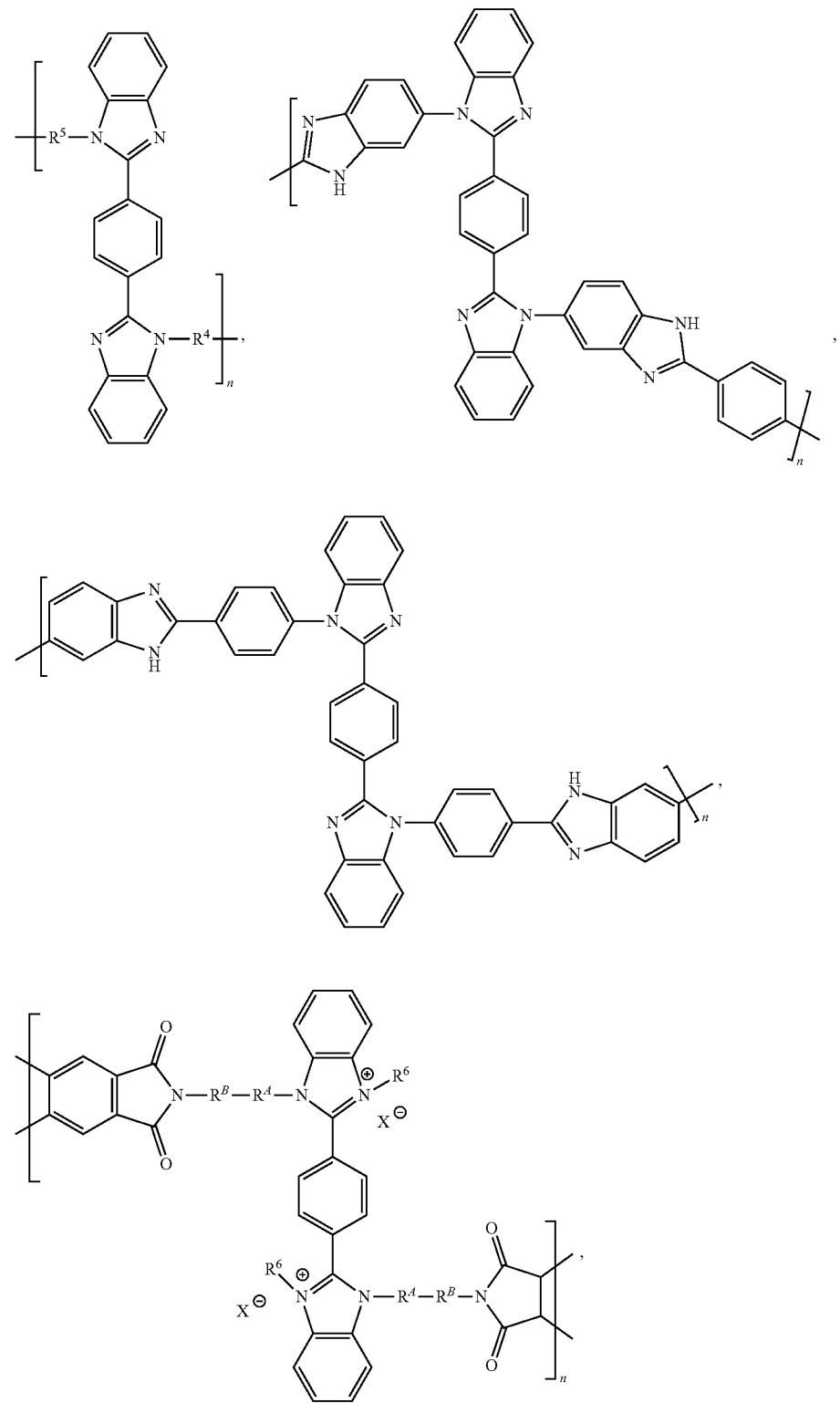

-continued

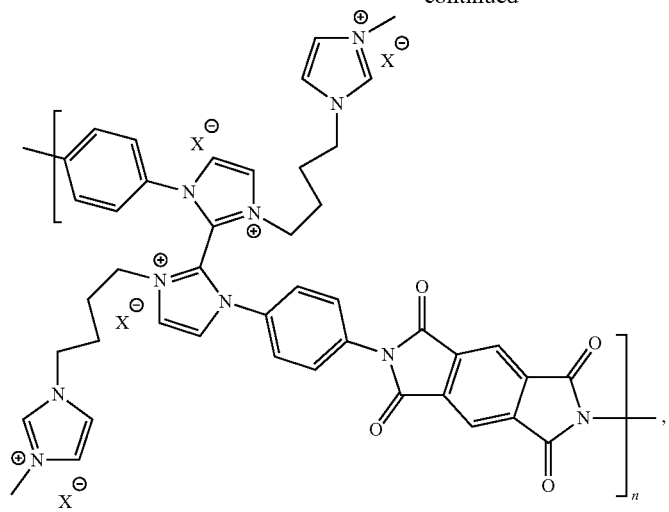

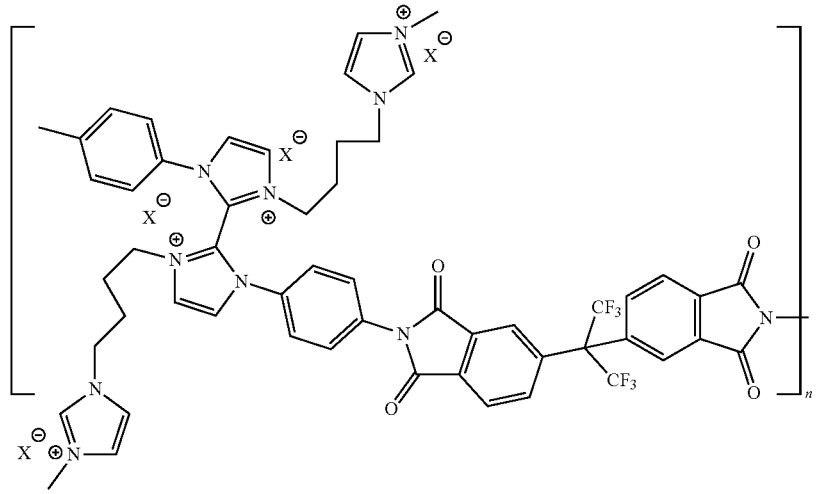

wherein R⁴ and R⁵ are, independently, $[R^{A'}-R^{B'}-R^{C'}]_m$, wherein $R^{A'}$, $R^{B'}$, $R^{C'}$, $R^A$, and $R^B$, each independent of the other selected from null, carboxyl group, hydroxy group, $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, $C_6$-$C_{14}$ aryloxy, $C_3$-$C_{10}$ cycloalkyl, or $C_3$-$C_{10}$ cycloalkenyl, heterocycloalkyl, polyester, imide, cyclic imide, imidazole, polysulfone, poly(aryl ether ketone), and wherein $R^A$, $R^B$, and $R^C$, are each independently of each other optionally substituted with $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, carbonyl, ester, ether, halide, carboxyl, hydroxy, nitro, cyano, silyl, sulfo-oxo, sulfonyl, sulfone, sulfoxide, thiol, or phosphonyl; and wherein any of $R^{A'}$, $R^{B'}$ or $R^{C'}$ are optionally the same; wherein at least one of $R^{A'}$, $R^{B'}$, and $R^{C'}$ is not null; or wherein at least one of $R^A$ or $R^B$ is not null, wherein m is an integer from 1 to 100, and wherein n is an integer from 1 to 100,000.

Also disclosed herein is a method comprising: a condensation polymerization of reactants wherein the reactants comprise one or more monomers and wherein at least one monomer has a general formula (II)

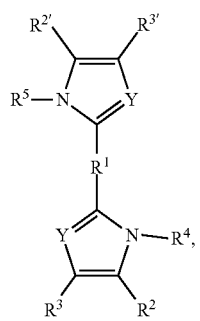

wherein, $R^1$ is selected from null, $C_1$-$C_{10}$ alkyl, $C_1$-$C_{10}$ perfluoroalkyl, $C_6$-$C_{14}$ aryl, or $C_1$-$C_{13}$ heteroaryl;

$R^2$, $R^{2'}$, $R^3$, and $R^{3'}$ are, each independent of the other, selected from hydrogen, $C_1$-$C_{10}$ alkyl, $C_1$-$C_{10}$ alkoxy, $C_6$-$C_{14}$ aryl, $C_1$-$C_{13}$ heteroaryl, or $C_6$-$C_{14}$ aryloxy, wherein each of $R^2$, $R^{2'}$, $R^3$, or $R^{3'}$ independent of the other, is optionally substituted with $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, amino, carbonyl, ester, ether, halide, carboxyl, hydroxy, nitro, cyano, silyl, sulfo-oxo, sulfonyl, sulfone, sulfoxide, thiol, or phosphonyl; or wherein R² and R³ together form a 6 membered ring containing 6 carbon atoms; and/or wherein R²' and R³' together form a 6 membered ring containing 6 carbon atoms; and wherein R² and R²' are the same or different; wherein R³ and R³' are the same or different;

R⁴ and R⁵ are independently [R$^{A'}$—R$^{B'}$—R$^{C'}$]$_m$, wherein R$^{A'}$, R$^{B'}$, and R$^{C'}$, each independent of the other, selected from null, hydrogen, hydroxy group, an amino group, $C_1$-$C_{10}$ alkyl, $C_1$-$C_{10}$ alkoxy, carboxyl group, $C_2$-$C_{10}$ alkenyl, $C_2$-$C_{10}$ alkynyl, $C_6$-$C_{14}$ aryl, $C_1$-$C_{13}$ heteroaryl, $C_6$-$C_{14}$ aryloxy, $C_3$-$C_{10}$ cycloalkyl, or $C_3$-$C_{10}$ cycloalkenyl, polyester, polysulfone, poly(aryl ether ketone), and wherein R$^{A'}$, R$^{B'}$, and R$^{C'}$, are each independently of each other optionally substituted with $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, carbonyl, ester, ether, halide, carboxyl, hydroxy, nitro, cyano, silyl, sulfo-oxo, sulfonyl, sulfone, sulfoxide, thiol, or phosphonyl; wherein any of R$^{A'}$, R$^{B'}$ or R$^{C'}$ are optionally the same, and wherein m is an integer from 1 to 100; and Y is N or N⁺—R⁶, wherein R⁶ is selected from hydrogen, $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, or $C_6$-$C_{14}$ aryloxy, wherein R⁶ is optionally substituted with $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, imide, cyclic imide, imidazole, imidazolium cation, carbonyl, ester, ether, halide, carboxyl, hydroxy, nitro, cyano, silyl, sulfo-oxo, sulfonyl, sulfone, sulfoxide, thiol, or phosphonyl.

In certain aspects, disclosed are methods wherein the at least one monomer is selected from:

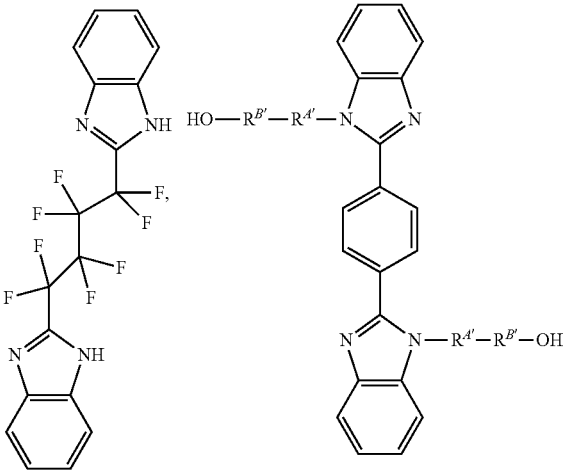

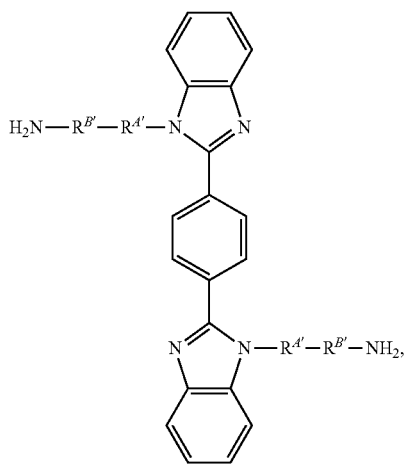

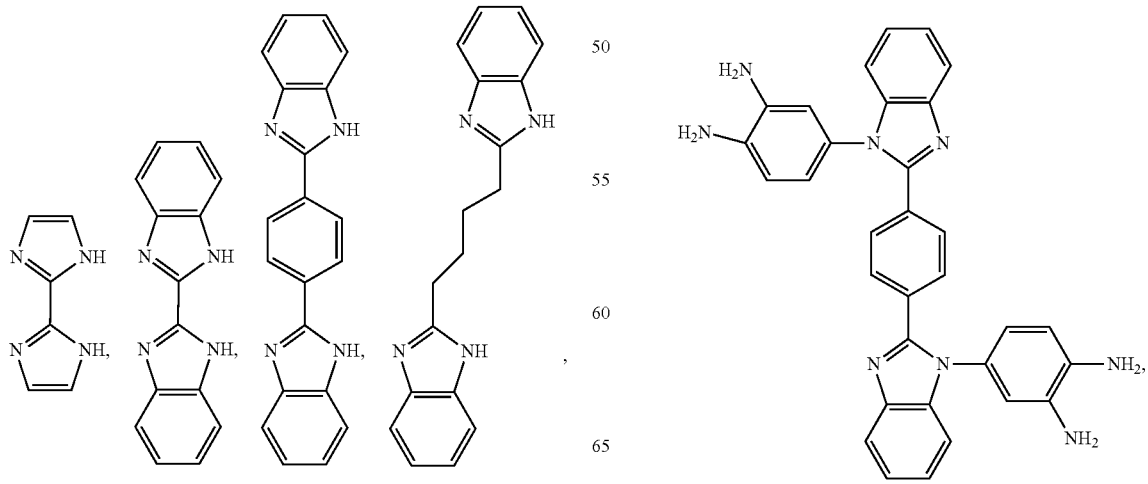

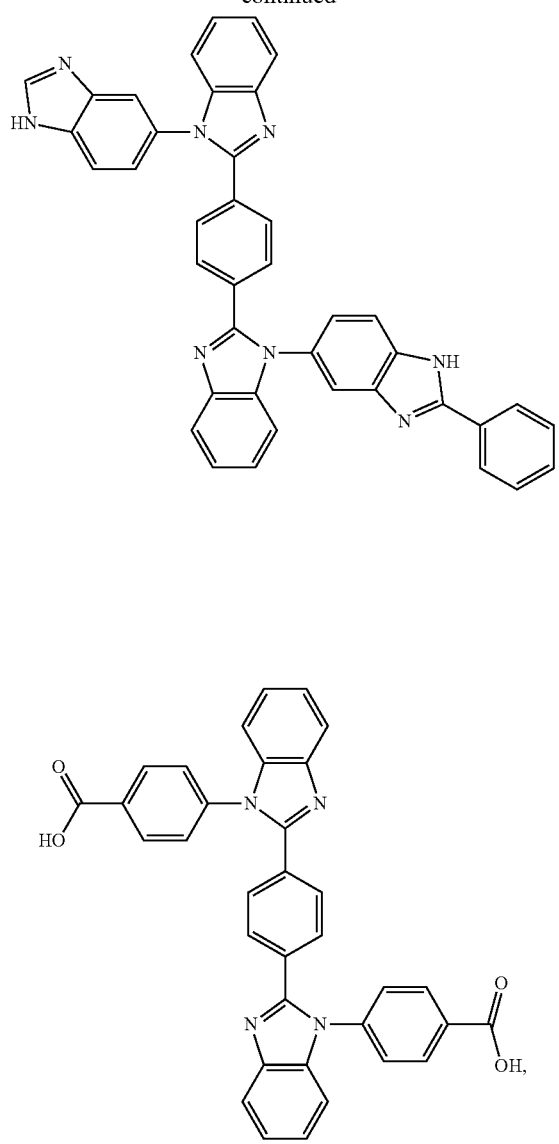

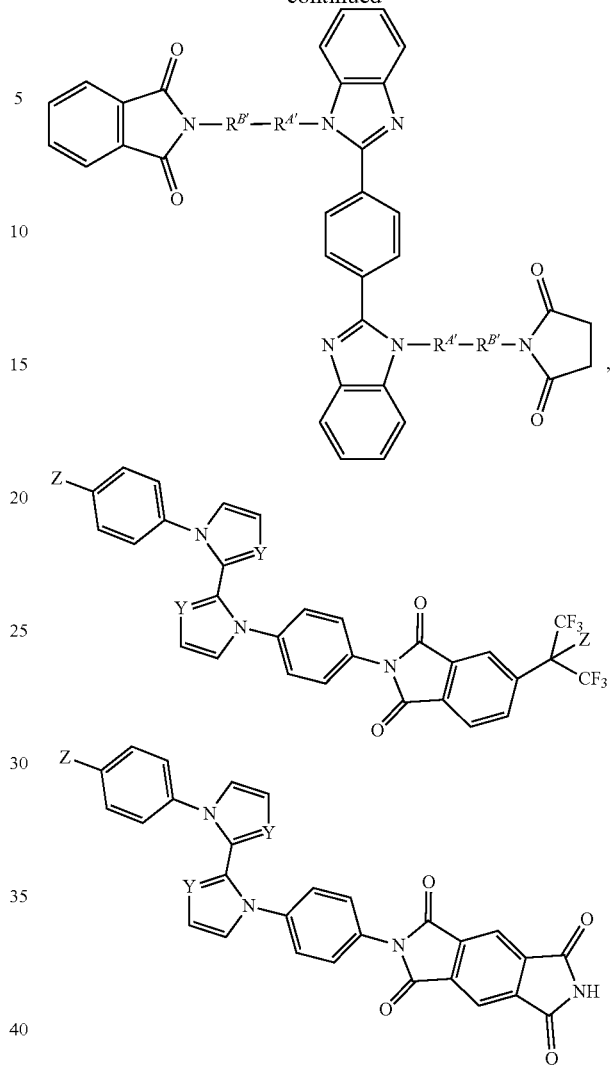

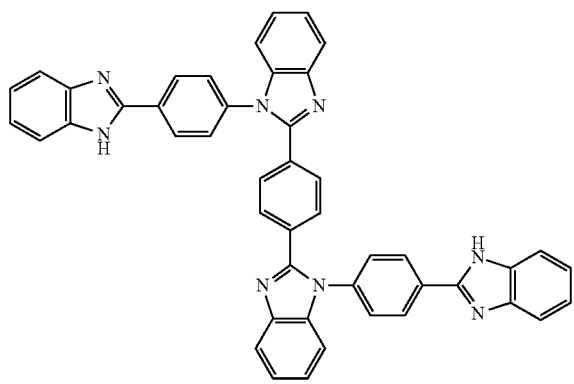

wherein $R^{A'}$ and $R^{B'}$, each independent of the other selected from null, carboxyl group, hydroxy group, $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, $C_6$-$C_{14}$ aryloxy, $C_3$-$C_{10}$ cycloalkyl, or $C_3$-$C_{10}$ cycloalkenyl, heterocycloalkyl, imide, cyclic imide, imidazole, polyester, polysulfone, poly(aryl ether ketone), and wherein $R^{A'}$ and $R^{B'}$, are each independently of each other optionally substituted with $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, carbonyl, ester, ether, halide, carboxyl, hydroxy, nitro, cyano, silyl, sulfo-oxo, sulfonyl, sulfone, sulfoxide, thiol, or phosphonyl; and wherein at least one of $R^{A'}$ and $R^{B'}$ is not null, and wherein $R^A$ and $R^{A'}$ and $R^B$ and $R^{B'}$ are the same; and wherein Z is selected from hydrogen, OH, or $NH_2$; and Y is N or $N^+$—$R^6$, wherein $R^6$ is selected from hydrogen, $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, or $C_6$-$C_{14}$ aryloxy, wherein $R^6$ is optionally substituted with $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, imide, cyclic imide, imidazole, imidazolium cation, carbonyl, ester, ether, halide, carboxyl, hydroxy, nitro, cyano, silyl, sulfo-oxo, sulfonyl, sulfone, sulfoxide, thiol, or phosphonyl.

Also, in certain aspects, disclosed herein are the methods wherein the condensation polymerization forms a composition of a general formula (III):

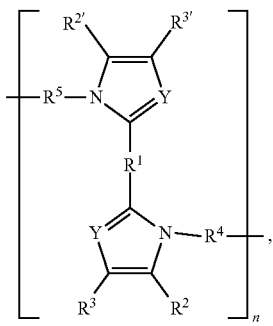

(III)

wherein,
- $R^1$ is selected from null, $C_1$-$C_{10}$ alkyl, $C_1$-$C_{10}$ perfluoroalkyl, $C_6$-$C_{14}$ aryl, or $C_1$-$C_{13}$ heteroaryl;
- $R^2$, $R^{2'}$, $R^3$, and $R^{3'}$ are, each independent of the other, selected from hydrogen, $C_1$-$C_{10}$ alkyl, $C_1$-$C_{10}$ alkoxy, $C_6$-$C_{14}$ aryl, $C_1$-$C_{13}$ heteroaryl, $C_6$-$C_{14}$ aryloxy, wherein each of $R^2$, $R^{2'}$, $R^3$, or $R^{3'}$ independent of the other, is optionally substituted with $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, amino, carbonyl, ester, ether, halide, carboxyl, hydroxy, nitro, cyano, silyl, sulfo-oxo, sulfonyl, sulfone, sulfoxide, thiol, or phosphonyl; or wherein $R^2$ and $R^3$ together form a 6 membered ring containing 6 carbon atoms; and/or wherein $R^{2'}$ and $R^{3'}$ together form a 6 membered ring containing 6 carbon atoms; and
- wherein $R^2$ and $R^{2'}$ are the same or different;
- wherein $R^3$ and $R^{3'}$ are the same or different;
- $R^4$ and $R^5$ are, independently, $[R^A{-}R^B{-}R^C]_m$, wherein $R^A$, $R^B$, and $R^C$, each independent of the other selected from null, carboxyl group, hydroxy group, $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, $C_6$-$C_{14}$ aryloxy, $C_3$-$C_{10}$ cycloalkyl, or $C_3$-$C_{10}$ cycloalkenyl, heterocycloalkyl, imide, cyclic imide, imidazole, polyester, polysulfone, poly(aryl ether ketone), and wherein $R^A$, $R^B$, and $R^C$, are each independently of each other optionally substituted with $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, carbonyl, ester, ether, halide, carboxyl, hydroxy, nitro, cyano, silyl, sulfo-oxo, sulfonyl, sulfone, sulfoxide, thiol, or phosphonyl; wherein any of $R^A$, $R^B$, or $R^C$ are the same or different; and wherein at least one of $R^A$, $R^B$, and $R^C$ is not null; wherein m is an integer from 1 to 100; wherein n is an integer from 1 to 100,000 and Y is N or $N^+{-}R^6$, wherein $R^6$ is selected from hydrogen, $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, or $C_6$-$C_{14}$ aryloxy, wherein $R^6$ is optionally substituted with $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, imide, imidazole, cyclic imide, carbonyl, ester, ether, halide, carboxyl, hydroxy, nitro, cyano, silyl, sulfo-oxo, sulfonyl, sulfone, sulfoxide, thiol, or phosphonyl.

Additional advantages will be set forth, in part, in the detailed figures and claims which follow, and in part will be derived from the detailed description or can be learned by practice of the invention. The advantages described below will be realized and attained by means of the elements and combinations particularly pointed out in the appended claims. It is to be understood that both the foregoing general description and the following detailed description are exemplary and explanatory only and are not restrictive.

DETAILED DESCRIPTION

The materials, compounds, compositions, and methods described herein may be understood more readily by reference to the following detailed description of specific aspects of the disclosed subject matter, the Figures, and the Examples included therein.

Before the present materials, compounds, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

Definitions

As used herein, the terms "optional" or "optionally" means that the subsequently described event or circumstance can or cannot occur and that the description includes instances where said event or circumstance occurs and instances where it does not.

It is appreciated that certain features of the disclosure, which are, for clarity, described in the context of separate aspects, can also be provided in combination in a single aspect. Conversely, various features of the disclosure, which are, for brevity, described in the context of a single aspect, can also be provided separately or in any suitable subcombination.

As used in the description and the appended claims, the singular forms "a," "an," and "the" include plural referents unless the context clearly dictates otherwise. Thus, for example, reference to "a composition" includes mixtures of two or more such compositions, reference to "a monomer" includes mixtures of two or more such monomers and the like.

It is also to be understood that the terminology used herein is for the purpose of describing particular aspects only and is not intended to be limiting. As used in the specification and the claims, the term "comprising" can include the aspects "consisting of" and "consisting essentially of."

For the terms "for example" and "such as," and grammatical equivalences thereof, the phrase "and without limitation" is understood to follow unless explicitly stated otherwise.

As used herein, the term "substituted" means that a hydrogen atom is removed and replaced by a substituent. It is contemplated to include all permissible substituents of organic compounds. As used herein, the phrase "optionally substituted" means unsubstituted or substituted. It is to be understood that substitution at a given atom is limited by valency. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valencies of the heteroatoms. This disclosure is not intended to be limited in any manner by the permissible substituents of organic compounds. Also, the terms "substitution" or "substituted with" include the implicit proviso that such substitution is in accordance with the permitted valence of the substituted atom and the substituent and that the substitution results in a stable compound, e.g., a compound that does not spontaneously undergo transformation such as by rearrangement, cyclization, elimination, etc. In still further aspects, it is understood that when the disclosure describes a group being substituted, it means that the group is substituted with one or more (i.e., 1, 2, 3, 4, or 5) groups as allowed by valence selected from alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

AH compounds, and salts thereof, can be found together with other substances such as water and solvents (e.g., hydrates and solvates).

Compounds provided herein also can include tautomeric forms. Tautomeric forms result from the swapping of a single bond with an adjacent double bond together with the concomitant migration of a proton. Tautomeric forms include prototropic tautomers that are isomeric protonation states having the same empirical formula and total charge. Example prototropic tautomers include ketone-enol pairs, amide-imidic add pairs, lactam lactim pairs, enamine imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds provided herein can also include all isotopes of atoms occurring in the intermediates or final compounds. Isotopes include those atoms having the same atomic number but different mass numbers. For example, isotopes of hydrogen include hydrogen, tritium, and deuterium.

Also provided herein are salts of the compounds described herein. It is understood that the disclosed salts can refer to derivatives of the disclosed compounds wherein the parent compound is modified by converting an existing acid or base moiety to its salt form. Examples of the salts include, but are not limited to, mineral or organic acid salts of basic residues such as amines; alkali or organic salts of acidic residues such as carboxylic acids; and the like. The salts of the compounds provided herein include the conventional non-toxic salts of the parent compound formed, for example, from non-toxic inorganic or organic acids. The salts of the compounds provided herein can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent or in a mixture of the two. In various aspects, nonaqueous media like ether, ethyl acetate, alcohols (e.g., methanol, ethanol, isopropanol, or butanol) or acetonitrile (ACN) can be used.

In various aspects, the compounds provided herein, or salts thereof, are substantially isolated. By "substantially isolated" is meant that the compound is at least partially or substantially separated from the environment in which it was formed or detected. Partial separation can include, for example, a composition enriched in the compounds provided herein. Substantial separation can include compositions containing at least about 50%, at least about 60%, at least about 70%, at least about 80%, at least about 90%, at least about 95%, at least about 97%, or at least about 99% by weight of the compounds provided herein, or salt thereof. Methods for isolating compounds and their salts are routine in the art.

As used herein, chemical structures that contain one or more stereocenters depicted with dashed and bold bonds are meant to indicate absolute stereochemistry of the stereocenter(s) present in the chemical structure. As used herein, bonds symbolized by a simple line do not indicate a stereopreference. Unless otherwise indicated to the contrary, chemical structures, which include one or more stereocenters, illustrated herein without indicating absolute or relative stereochemistry encompass all possible stereoisomeric forms of the compound (e.g., diastereomers and enantiomers) and mixtures thereof. Structures with a single bold or dashed line and at least one additional simple line encompass a single enantiomeric series of all possible diastereomers.

The resolution of racemic mixtures of compounds can be carried out using appropriate methods. An exemplary method includes fractional recrystallization using a chiral resolving acid that is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid, or the various optically active camphorsulfonic acids such as camphorsulfonic acid. Other resolving agents suitable for fractional crystallization methods include stereoisomerically pure forms of methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent compositions can be determined by one skilled in the art.

The expressions "ambient temperature" and "room temperature" as used herein are understood in the art and refer generally to a temperature, e.g., a reaction temperature, that is about the temperature of the room in which the reaction is carried out, for example, a temperature from about 20° C. to about 30° C.

"$R^1$," "$R^2$," "$R^3$," "$R^4$," etc., are used herein as generic symbols to represent various specific substituents. These symbols can be any substituent, not limited to those disclosed herein, and when they are defined to be certain substituents in one instance, they can, in another instance, be defined as some other substituents.

At various places in the present specification, divalent linking substituents are described. It is specifically intended that each divalent linking substituent includes both the forward and backward forms of the linking substituent. For example, —NR(CR'R")$_n$-includes both —NR(CR'R")$_n$— and —(CR'R")$_n$NR—. Where the structure dearly requires a linking group, the Markush variables listed for that group are understood to be linking groups.

The term "n-membered," where n is an integer, typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

Throughout the definitions, the term "$C_n$-$C_m$" indicates a range that includes the endpoints, wherein n and in are integers and indicate the number of carbons. Examples include, without limitation, $C_1$-$C_4$, $C_1$-$C_6$, and the like.

The term "aliphatic" as used herein refers to a non-aromatic hydrocarbon group and includes branched and unbranched, alkyl, alkenyl, or alkynyl groups. As used herein, the term "$C_n$-$C_m$ alkyl," employed alone or in combination with other terms, refers to a saturated hydrocarbon group that may be straight-chain or branched, having n to m carbons. Examples of alkyl moieties include, but are not limited to, chemical groups such as methyl, ethyl, n-propyl, isopropyl, n-butyl, tert-butyl, isobutyl, sec-butyl; higher homologs such as 2-methyl-l-butyl, n-pentyl, 3-pentyl, n-hexyl, 1,2,2-trimethylpropyl, heptyl, octyl, nonyl, decyl, dodecyl, tetradecyl, hexadecyl, eicosyl, tetracosyl, and the like. In various aspects, the alkyl group contains from 1 to 24 carbon atoms, from 1 to 12 carbon atoms, from 1 to 10 carbon atoms, from 1 to 8 carbon atoms, from 1 to 6 carbon atoms, from 1 to 4 carbon atoms; from 1 to 3 carbon atoms, or 1 to 2 carbon atoms. The alkyl group can also be substituted or unsubstituted. Throughout the specification, "alkyl" is generally used to refer to both unsubstituted alkyl groups and substituted alkyl groups; however, substituted alkyl groups are also specifically referred to herein by identifying the specific substituent(s) on the alkyl group. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below and the like. When "alkyl" is used in one instance, and a specific term such as "alkylalcohol" is used in another, it is not meant to imply that the term "alkyl" does not also refer to specific terms such as "alkylalcohol" and the like.

As used herein, "$C_n$-$C_m$ alkenyl" refers to an alkyl group having one or more double carbon-carbon bonds and having n to in carbons. Example alkenyl groups include, but are not limited to, ethenyl, n-propenyl, isopropenyl, n-butenyl, seobutenyl, and the like. In various aspects, the alkenyl moiety contains 2 to 6, 2 to 4, or 2 to 3 carbon atoms. Asymmetric structures such as $(R^1R^2)C=C(R^3R^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, cyano, silyl, sulfo-oxo, sulfonyl, sulfone, sulfoxide, thiol, thiol, or phosphonyl, as described below.

As used herein, "$C_n$-$C_m$ alkynyl" refers to an alkyl group having one or more triple carbon-carbon bonds and having n to m carbons. Exemplary alkynyl groups include, but are not limited to, ethynyl, propyn-1-yl, propyn-2-yl, and the like. In various aspects, the alkynyl moiety contains 2 to 6, 2 to 4, or 2 to 3 carbon atoms. The alkynyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, cyano, silyl, sulfo-oxo, sulfonyl, sulfone, sulfoxide, thiol, or phosphonyl, as described below.

As used herein, the term "$C_n$-$C_m$ alkylene," employed alone or in combination with other terms, refers to a divalent alkyl linking group having n to m carbons. Examples of alkylene groups include, but are not limited to, ethan-1,2-diyl, propan-1,3-diyl, propan-1,2-diyl, butan-1,4-diyl, butan-1,3-diyl, butan-1,2-diyl, 2-methyl-propan-1,3-diyl, and the like. In various aspects, the alkylene moiety contains 2 to 6, 2 to 4, 2 to 3, 1 to 6, 1 to 4, or 1 to 2 carbon atoms.

As used herein, the term "$C_n$-$C_m$ alkoxy," employed alone or in combination with other terms, refers to a group of formula —O-alkyl, wherein the alkyl group has n to m carbons. Exemplary alkoxy groups include methoxy, ethoxy, propoxy (e.g., w-propoxy and isopropoxy), tert-butoxy, and the like. In various aspects, the alkyl group has 1 to 6, 1 to 4, or 1 to 3 carbon atoms.

The terms "amine" or "amino" as used herein are represented by the formula —NR$^1$R$^2$, where R$^1$ and R$^2$ can each be substitution group as described herein, such as hydrogen, an alkyl, halogenated alkyl, alkenyl, alkynyl, aryl, heteroaryl, cycloalkyl, cycloalkenyl, heterocycloalkyl, or heterocycloalkenyl group described above. "Amido" is —C(O)NR$^1$R$^2$.

As used herein, the term "$C_n$-$C_m$ alkylamino" refers to a group of formula —NH(alkyl), wherein the alkyl group has n to m carbon atoms. In various aspects, the alkyl group has 1 to 6, 1 to 4, or 1 to 3 carbon atoms.

As used herein, the term "$C_n$-$C_m$ alkoxycarbonyl" refers to a group of formula —C(O)O-alkyl, wherein the alkyl group has n to m carbon atoms. In various aspects, the alkyl group has 1 to 6, 1 to 4, or 1 to 3 carbon atoms.

As used herein, the term "$C_n$-$C_m$ alkylcarbonyl" refers to a group of formula —C(O)-alkyl, wherein the alkyl group has n to m carbon atoms. In various aspects, the alkyl group has 1 to 6, 1 to 4, or 1 to 3 carbon atoms.

As used herein, the term "$C_n$-$C_m$ alkylcarbonylamino" refers to a group of formula —NHC(O)-alkyl, wherein the alkyl group has n to m carbon atoms. In various aspects, the alkyl group has 1 to 6, 1 to 4, or 1 to 3 carbon atoms.

As used herein, the term "$C_n$-$C_m$ alkylsulfonylamino" refers to a group of formula —NHS(O)$_2$-alkyl, wherein the alkyl group has n to m carbon atoms. In various aspects, the alkyl group has 1 to 6, 1 to 4, or 1 to 3 carbon atoms.

The term "aldehyde" as used herein is represented by the formula —C(O)H. Throughout this specification, "C(O)" or "CO" is a shorthand notation for C=O, which is also referred to herein as a "carbonyl."

The term "carboxylic acid" as used herein is represented by the formula —C(O)OH. A "carboxylate" or "carboxyl" group as used herein is represented by the formula —C(O)O$^-$.

The term "ester" as used herein is represented by the formula —OC(O)R$^1$ or —C(O)OR$^1$, where R$^1$ can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula R$^1$OR$^2$, where R$^1$ and R$^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ketone" as used herein is represented by the formula R$^1$C(O)R$^2$, where R$^1$ and R$^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

As used herein, the term "aminosulfonyl" refers to a group of formula —S(O)$_2$NH$_2$.

As used herein, the term "$C_n$-$C_m$ alkylaminosulfonyl" refers to a group of formula —S(O)$_2$NH(alkyl), wherein the alkyl group has n to in carbon atoms. In various aspects, the alkyl group has 1 to 6, 1 to 4, or 1 to 3 carbon atoms.

As used herein, the term "di($C_n$-$C_m$ alkyl)aminosulfonyl" refers to a group of formula —S(O)$_2$N(alkyl)$_2$, wherein each alkyl group independently has n to m carbon atoms. In various aspects, each alkyl group has, independently, 1 to 6, 1 to 4, or 1 to 3 carbon atoms.

As used herein, the term "aminosulfonylamino" refers to a group of formula —NHS(O)$_2$NH$_2$.

As used herein, the term "$C_n$-$C_m$ alkylaminosulfonylamino" refers to a group of formula —NHS(O)$_2$NH(alkyl), wherein the alkyl group has n to m carbon atoms. In various aspects, the alkyl group has 1 to 6, 1 to 4, or 1 to 3 carbon atoms.

As used herein, the term "di($C_n$-$C_m$ alkyl)aminosulfonylamino" refers to a group of formula —NHS(O)$_2$N(alkyl)$_2$, wherein each alkyl group independently has n to m carbon atoms. In various aspects, each alkyl group has, independently, 1 to 6, 1 to 4, or 1 to 3 carbon atoms.

As used herein, the term "aminocarbonylamino," employed alone or in combination with other terms, refers to a group of formula —NHC(O)NH$_2$.

As used herein, the term "$C_n$-$C_m$ alkylaminocarbonylamino" refers to a group of formula —NHC(O)NH(alkyl), wherein the alkyl group has n to m carbon atoms. In various aspects, the alkyl group has 1 to 6, 1 to 4, or 1 to 3 carbon atoms.

As used herein, the term "di($C_n$-$C_m$ alkyl)aminocarbonylamino" refers to a group of formula —NHC(O)N(alkyl)$_2$, wherein each alkyl group independently has n to m carbon atoms. In various aspects, each alkyl group has, independently, 1 to 6, 1 to 4, or 1 to 3 carbon atoms.

As used herein, the term "$C_n$-$C_m$ alkylcarbamyl" refers to a group of formula —C(O)—NH(alkyl), wherein the alkyl group has n to m carbon atoms. In various aspects, the alkyl group has 1 to 6, 1 to 4, or 1 to 3 carbon atoms.

As used herein, the term "thio" refers to a group of formula —SH.

As used herein, the term "$C_n$-$C_m$ alkylthio" refers to a group of formula —S— alkyl, wherein the alkyl group has n to m carbon atoms. In various aspects, the alkyl group has 1 to 6, 1 to 4, or 1 to 3 carbon atoms.

As used herein, the term "$C_n$-$C_m$ alkylsulfinyl" refers to a group of formula —S(O)-alkyl, wherein the alkyl group has n to in carbon atoms. In various aspects, the alkyl group has 1 to 6, 1 to 4, or 1 to 3 carbon atoms.

As used herein, the term "$C_n$-$C_m$ alkylsulfonyl" refers to a group of formula —S(O)$_2$-alkyl, wherein the alkyl group has n to m carbon atoms. In various aspects, the alkyl group has 1 to 6, 1 to 4, or 1 to 3 carbon atoms.

As used herein, the term "carbamyl" to a group of formula —C(O)NH$_2$.

As used herein, the term "carbonyl" employed alone or in combination with other terms, refers to a —C(=O)— group, which may also be written as C(O).

As used herein, the term "carboxy" refers to a group of formula —C(O)OH.

As used herein, the term "($C_n$-$C_m$)($C_n$-$C_m$)amino" refers to a group of formula —N(alkyl)$_2$, wherein the two alkyl groups each has, independently, n to m carbon atoms. In various aspects, each alkyl group independently has 1 to 6, 1 to 4 or 1 to 3 carbon atoms.

As used herein, the term "di($C_n$-$C_m$-alkyl)carbamyl" refers to a group of formula —C(O)N(alkyl)$_2$, wherein the two alkyl groups each has, independently, n to m carbon atoms. In various aspects, each alkyl group independently has 1 to 6, 1 to 4, or 1 to 3 carbon atoms.

As used herein, "halogen" refers to F, Cl, Br, or I.

The term "hydroxyl" as used herein is represented by the formula —OH.

The term "cyano" as used herein is represented by the formula —CN.

The term "nitro" as used herein is represented by the formula —NO$_2$.

The term "phosphonyl" is used herein to refer to the phospho-oxo group represented by the formula —P(O)(OR$^1$)$_2$, where R$^1$ can be absent, hydrogen, an alkyl, alkenyl, alkynyl, aryl, heteroaryl, cycloalkyl, or cycloalkenyl.

The term "silyl" as used herein is represented by the formula —SiR$^1$R$^2$R$^3$, where R$^1$, R$^2$, and R$^3$ can be, independently, hydrogen, alkyl, halogenated alkyl, alkoxy, alkenyl, alkynyl, aryl, heteroaryl, cycloalkyl, cycloalkenyl, heterocycloalkyl, or heterocycloalkenyl group described above.

The term "sulfonyl" is used herein to refer to the sulfo-oxo group represented by the formula —S(O)$_2$R$^1$, where R$^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfonylamino" or "sulfonamide" as used herein is represented by the formula —S(O)$_2$NH—.

As used herein, "$C_n$-$C_m$ haloalkoxy" refers to a group of formula —O-haloalkyl having n to m carbon atoms. An example haloalkoxy group is OCF$_3$. In various aspects, the haloalkoxy group is fluorinated only. In various aspects, the alkyl group has 1 to 6, 1 to 4, or 1 to 3 carbon atoms.

As used herein, the term "$C_n$-$C_m$ haloalkyl," employed alone or in combination with other terms, refers to an alkyl group having from one halogen atom to 2s+1 halogen atoms, which may be the same or different, where "s" is the number of carbon atoms in the alkyl group, wherein the alkyl group has n to m carbon atoms. In various aspects, the haloalkyl group is fluorinated only. In various aspects, the alkyl group has 1 to 6, 1 to 4, or 1 to 3 carbon atoms.

As used herein, the term "amine base" refers to a mono-substituted amino group (i.e., primary amine base), di-substituted amino group (i.e., secondary amine base), or a tri-substituted amine group (i.e., tertiary amine base). Exemplary mono-substituted amine bases include methylamine, ethylamine, propylamine, butylamine, and the like. Example di-substituted amine bases include dimethylamine, diethylamine, dipropylamine, dibutylamine, pyrrolidine, piperidine, azepane, morpholine, and the like, hi various aspects, the tertiary amine has the formula $N(R')_3$, wherein each R' is independently $C_1$-$C_6$ alkyl, 3-10 member cycloalkyl, 4-10 membered heterocycloalkyl, 1-10 membered heteroaryl, and 5-10 membered aryl, wherein the 3-10 member cycloalkyl, 4-10 membered heterocycloalkyl, 1-10 membered heteroaryl, and 5-10 membered aryl is optionally substituted by 1, 2, 3, 4, 5, or 6 Ci-6 alkyl groups. Exemplary tertiary amine bases include trimethylamine, triethylamine, tripropylamine, triisopropylamine, tributylamine, tri-tert-butylamine, N,N-dimethylethanamine, N-ethyl-N-methylpropan-2-amine, N-ethyl-N-isopropylpropan-2-amine, morpholine, N-methylmorpholine, and the like. In various aspects, the term "tertiary amine base" refers to a group of formula $N(R)_3$, wherein each R is independently a linear or branched $C_{1-6}$ alkyl group.

As used herein, "cycloalkyl" refers to non-aromatic cyclic hydrocarbons, including cyclized alkyl and/or alkenyl groups. Cycloalkyl groups can include mono- or polycyclic (e.g., having 2, 3 or 4 fused rings) groups and spirocycles. Cycloalkyl groups can have 3, 4, 5, 6, 7, 8, 9, or 10 ring-forming carbons ($C_{3-10}$). Ring-forming carbon atoms of a cycloalkyl group can be optionally substituted by oxo or sulfido (e.g., C(O) or C(S)). Cycloalkyl groups also include cycloalkylidenes. Exemplary cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, and the like. In various aspects, cycloalkyl is cyclopropyl, cyclobutyl, cyclopentyl, cyclohexyl, cyclopentyl, or adamantyl. In various aspects, the cycloalkyl has 6-10 ring-forming carbon atoms. In various aspects, cycloalkyl is cyclohexyl or adamantyl. Also included in the definition of cycloalkyl are moieties that have one or more aromatic rings fused (i.e., having a bond in common with) to the cycloalkyl ring, for example, benzo or thienyl derivatives of cyclopentane, cyclohexane, and the like. A cycloalkyl group containing a fused aromatic ring can be attached through any ring-forming atom, including a ring-forming atom of the fused aromatic ring.

As used herein, "heterocycloalkyl" refers to non-aromatic monocyclic or polycyclic heterocycles having one or more ring-forming heteroatoms selected from O, N, or S. Included in heterocycloalkyl are monocyclic 4-, 5-, 6-, and 7-membered heterocycloalkyl groups. Heterocycloalkyl groups can also include spirocycles. Exemplary heterocycloalkyl groups include pyrrolidin-2-one, 1,3-isoxazolidin-2-one, pyranyl, tetrahydropuran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, benzazapene, and the like. Ring-forming carbon atoms and heteroatoms of a heterocycloalkyl group can be optionally substituted by oxo or sulfido (e.g., C(O), S(O), C(S), or $S(O)_2$, etc.). The heterocycloalkyl group can be attached through a ring-forming carbon atom or a ring-forming heteroatom. In various aspects, the heterocycloalkyl group contains 0 to 3 double bonds. In various aspects, the heterocycloalkyl group contains 0 to 2 double bonds. Also included in the definition of heterocycloalkyl are moieties that have one or more aromatic rings fused (i.e., having a bond in common with) to the cycloalkyl ring, for example, benzo or thienyl derivatives of piperidine, morpholine, azepine, etc. A heterocycloalkyl group containing a fused aromatic ring can be attached through any ring-forming atom, including a ring-forming atom of the fused aromatic ring. In various aspects, the heterocycloalkyl has 4-10, 4-7 or 4-6 ring atoms with 1 or 2 heteroatoms independently selected from nitrogen, oxygen, or sulfur and having one or more oxidized ring members.

The term "cycloalkenyl" as used herein is a non-aromatic carbon-based ring composed of at least three carbon atoms and containing at least one double bond, i.e., C=C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above and is included within the meaning of the term "cycloalkenyl," where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, cyano, silyl, sulfo-oxo, sulfonyl, sulfone, sulfoxide, thiol, or phosphonyl, as described herein.

The term "cyclic group" is used herein to refer to either aryl groups, non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups, and one or more non-aryl groups.

As used herein, the term "aryl," employed alone or in combination with other terms, refers to an aromatic hydrocarbon group, which may be monocyclic or polycyclic (e.g., having 2, 3 or 4 fused rings). The term "$C_{n-m}$ aryl" refers to an aryl group having from n to m ring carbon atoms. Aryl groups include, e.g., phenyl, naphthyl, anthracenyl, phenanthrenyl, indanyl, indenyl, and the like. In various aspects, aryl groups have from 6 to about 20 carbon atoms, from 6 to about 15 carbon atoms, or from 6 to about 10 carbon atoms. In various aspects, the aryl group is a substituted or unsubstituted phenyl.

As used herein, "heteroaryl" refers to a monocyclic or polycyclic aromatic heterocycle having at least one heteroatom ring member selected from sulfur, oxygen, phosphorus, and nitrogen. In various aspects, the heteroaryl ring has 1, 2, 3, or 4 heteroatom ring members independently selected from nitrogen, sulfur, and oxygen. In various aspects, any ring-forming N in a heteroaryl moiety can be an N-oxide. In various aspects, the heteroaryl has 5-10 ring atoms and 1, 2, 3 or 4 heteroatom ring members independently selected from nitrogen, sulfur, and oxygen. In various aspects, the heteroaryl has 5-6 ring atoms and 1 or 2 heteroatom ring members independently selected from nitrogen, sulfur, and oxygen. In various aspects, the heteroaryl is a five-membered or six-membered heteroaryl ring. A five-membered heteroaryl ring is a heteroaryl with a ring having five ring atoms wherein one or more (e.g., 1, 2, or 3) ring atoms are independently selected from N, O, and S. Exemplary five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl. A six-membered heteroaryl ring is a heteroaryl with a ring having six ring atoms wherein one or more (e.g.

1, 2, or 3) ring atoms are independently selected from N, O, and S. Exemplary six-membered ring heteroaryls are pyridyl, pyrazinyl, pyrimidinyl, triazinyl, and pyridazinyl.

The aryl or heteroaryl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, cyano, silyl, sulfo-oxo, sulfonyl, sulfone, sulfoxide, thiol, or phosphonyl, as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

At certain places, the definitions or aspects refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas an azetidin-3-yl ring is attached at the 3-position.

As used herein, the term "electron withdrawing group" (EWG), employed alone or in combination with other terms, refers to an atom or group of atoms substituted onto a π-system (e.g., substituted onto an aryl or heteroaryl ring) that draws electron density away from the π-system through induction (e.g., withdrawing electron density about a σ-bond) or resonance (e.g., withdrawing electron density about a π-bond or π-system). Example electron withdrawing groups include, but are not limited to, halo groups (e.g., fluoro, chloro, bromo, iodo), nitriles (e.g., —ON), carbonyl groups (e.g., aldehydes, ketones, carboxylic acids, acid chlorides, esters, and the like), nitro groups (e.g., —NO$_2$), haloalkyl groups (e.g., —CH$_2$F, —CHF$_2$, —CF$_3$, and the like), alkenyl groups (e.g., vinyl), alkynyl groups (e.g., ethynyl), sulfonyl groups (e.g., S(O)R, S(O)$_2$R), sulfonate groups (e.g., —SO$_3$H), and sulfonamide groups (e.g., S(O)N(R)$_2$, S(O)$_2$N(R)=), In various aspects, the electron withdrawing group is selected from the group consisting of halo, C$_2$-C$_6$ alkenyl, C$_2$-C$_6$ alkynyl, C$_1$-C$_3$ haloalkyl, ON, NO$_2$, C(=O)OR$^{al}$, C(=O)R$^{bl}$, C(=O)NR$^{cl}$R$^{dl}$, O(=O)SR$^{el}$, —NR$^{cl}$S(O)R$^{el}$, —NR$^{cl}$S(O)$_2$R$^{el}$, S(=O)R$^{el}$, S(=O)$_2$R$^{el}$, S(=O)NR$^{cl}$R$^{dl}$, S(=O)$_2$NR$^{cl}$R$^{dl}$, and P(O)(OR$^{al}$)$_2$. In various aspects, the electron withdrawing group is selected from the group consisting of C(=O)OR$^{al}$, C(=O)R$^{bl}$, C(=O)NR$^{cl}$R$^{dl}$, C(=O)SR$^{el}$, S(=O)R$^{el}$, S(=O)$_2$R$^{el}$, S(=O)NR$^{cl}$R$^{dl}$, and S(=O)$_2$NR$^{cl}$R$^{dl}$. In various aspects, the electron withdrawing group is O(=O)OR$^{al}$, In various aspects, the electron withdrawing group is C(=O)OR$^{al}$, wherein R$^{al}$, R$^{bl}$, R$^{cl}$, R$^{dl}$, and R$^{el}$ are independently selected at each occurrence from alkyl, alkenyl, alkynyl, cycloalkyl, cycloalkenyl, heterocycloalkyl, aryl, or heteroaryl, each of which R$^{al}$, R$^{bl}$, R$^{cl}$, R$^{dl}$, or R$^{el}$ may be optionally substituted with one or more substituents as described herein.

"R$^1$," "R$^2$," "R$^3$," "R$^n$," etc., where n is some integer, as used herein can, independently, possess one or more of the groups listed above. For example, if R$^1$ is a straight chain alkyl group, one of the hydrogen atoms of the alkyl group can optionally be substituted with a hydroxyl group, an alkoxy group, an amine group, an alkyl group, a halide, and the like. Depending upon the groups that are selected, a first group can be incorporated within the second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

Dashed lines in a chemical structure are used to indicate that a bond may be present or absent or that it may be a delocalized bond between the indicated atoms.

As used herein, the term "ionic liquid" refers to a salt in which the ions are poorly coordinated, and as a result, the salts are present in a liquid state at a temperature below about 150° C., for example, below about 120° C., about 100° C., about 80° C., about 60° C., about 40° C., about 25° C., or even below about 20° C. However, it is further understood that the ionic liquids can be present as solids at other temperature ranges or points. Since the disclosed ionic liquid compositions are liquid, and thus not crystalline solids, at a given temperature, the disclosed compositions do not suffer from the problems of polymorphism associated with crystalline solids. An ionic liquid is not considered a mere solution containing ions as solutes dissolved therein. In ionic liquids, at least one ion has a delocalized charge, and at least one component is organic. It is understood that while the cation can have an impact on the properties of the ionic liquid and often define its stability, the anion can have an impact on the chemistry and functionality of the ionic liquid. Some exemplary and unlimiting cations can comprise imidazolium, pyridinium, pyrrolidinium, phosphonium, ammonium, sulfonium, or any combination thereof. Some exemplary and unlimiting anions can comprise alkylsulfate, tosylate, methanesulfonate, bis(trifluoromethylesulfonyl) imide, hexafluorophosphate, tetrafluoroborate, halide, or any combination thereof.

Preparation of the compounds described herein can involve a reaction in the presence of an add or a base. Example acids can be inorganic or organic acids and include, but are not limited to, strong and weak acids. Example acids include, but are not limited to, hydrochloric acid, hydrobromic acid, sulfuric acid, phosphoric acid, p-toluenesulfonic acid, 4-nitrobenzoic acid, methanesulfonic acid, benzenesulfonic acid, trifluoroacetic acid, and nitric acid. Example weak acids include, but are not limited to, acetic acid, propionic acid, butanoic acid, benzoic acid, tartaric acid, pentanoic acid, hexanoic acid, heptanoic acid, octanoic acid, nonanoic acid, and decanoic acid. Example bases include; without limitation, lithium hydroxide, sodium hydroxide, potassium hydroxide, lithium carbonate, sodium carbonate, potassium carbonate, sodium bicarbonate, and amine bases. Example strong bases include, but are not limited to, hydroxide, alkoxides, metal amides, metal hydrides, metal dialkylamides, and arylamines, wherein; alkoxides include lithium, sodium and potassium salts of methyl, ethyl and t-butyl oxides; metal amides include sodium amide, potassium amide, and lithium amide; metal hydrides include sodium hydride, potassium hydride, and lithium hydride; and metal dialkylamides include lithium, sodium, and potassium salts of methyl, ethyl, n-propyl, iso-propyl, n-butyl, t-butyl, trimethylsilyl, and cyclohexyl substituted amides (e.g., lithium N-isopropylcyclohexylamide).

The following abbreviations may be used herein: AcOH (acetic acid); aq. (aqueous); atm. (atmosphere(s)); Br$_2$ (bromine); Bn (benzyl); calc. (calculated); d (doublet); dd (doublet of doublets); DCM (dichloromethane); DMF (N,N-dimethylformamide); Et (ethyl); Et$_2$O (diethyl ether);

EtOAc (ethyl acetate); EtOH (ethanol); EWG (electron withdrawing group); g (gram(s)); h (hour(s)); HCl (hydrochloric acid/hydrogen chloride); HPLC (high performance liquid chromatography); $H_2SO_4$ (sulfuric acid); Hz (hertz); (iodine); IPA (isopropyl alcohol); J (coupling constant); KOH (potassium hydroxide); $K_3PO_4$ (potassium phosphate); LCMS (liquid chromatography-mass spectrometry); GC (gas chromatography), LUCA (lithium N-isopropylcyclohexylamide); m (multiplet); M (molar); MS (Mass spectrometry); Me (methyl); MeCN (acetonitrile); MeOH (methanol); mg (milligram(s)); min, (minutes(s)); mL (milliliter(s)); mmol (millimole(s)); N (normal); $NaBH_4CN$ (sodium cyanoborohydride); NHP (N-heterocyclic phosphine); NHP-Cl (N-heterocyclic phosphine chloride); $Na_2CO_3$ (sodium carbonate); $NaHCO_3$ (sodium bicarbonate); NaOH (sodium hydroxide); $Na_2SO_4$ (sodium sulfate); nM (nanomolar); NMR (nuclear magnetic resonance spectroscopy); PCb (trichlorophosphine); PMP (4-methoxyphenyl); RP-HPLC (reverse phase high performance liquid chromatography); t (triplet or tertiary); t-Bu (tert-butyl); TEA (triethylamine); TFA (trifluoroacetic add); THF (tetrahydrofuran); TLC (thin layer chromatography); μg (microgram(s)); μL (microliter(s)); μM (micromolar); wt % (weight percent).

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements. Furthermore, when numerical ranges of varying scope are set forth herein, it is contemplated that any combination of these values inclusive of the recited values may be used. Further, ranges can be expressed herein as from "about" one particular value and/or to "about" another particular value. When such a range is expressed, another aspect includes from the one particular value and/or to the other particular value.

Similarly, when values are expressed as approximations, by use of the antecedent "about," it will be understood that the particular value forms another aspect. It will be further understood that the endpoints of each of the ranges are significant both in relation to the other endpoint and independently of the other endpoint. Unless stated otherwise, the term "about" means within 5% (e.g., within 2% or 1%) of the particular value modified by the term "about."

As used herein, the term "composition" is intended to encompass a product comprising the specified ingredients in the specified amounts, as well as any product which results, directly or indirectly, from a combination of the specified ingredients in the specified amounts.

References in the specification and concluding claims to parts by weight of a particular element or component in a composition denotes the weight relationship between the element or component and any other elements or components in the composition or article for which a part by weight is expressed. Thus, in a mixture containing 2 parts by weight of component X and 5 parts by weight, component Y, X and Y are present at a weight ratio of 2:5, and are present in such ratio regardless of whether additional components are contained in the mixture.

A weight percent (wt. %) of a component, unless specifically stated to the contrary, is based on the total weight of the formulation or composition in which the component is included.

As used herein, the terms "substantially" refers to at least about 80%, at least about 85%, at least about 90%, at least about 91%, at least about 92%, at least about 93%, at least about 94%, at least about 95%, at least about 96%, at least about 97%, at least about 98%, at least about 99%, or about 100% of the stated property, component, composition, or other condition for which substantially is used to characterize or otherwise quantify an amount.

It is further understood that certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co. (Milwaukee, WI), Acros Organics (Morris Plains, NJ), Fisher Scientific (Pittsburgh, PA), Sigma (St. Louis, MO), or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989). Other materials, such as the ligands, disclosed herein can be obtained from commercial sources.

Reference will now be made in detail to specific aspects of the disclosed materials, compounds, compositions, articles, and methods, examples of which are illustrated in the accompanying Examples and Figures.

Compositions

As summarized above, disclosed herein are the compositions having (ultra)high performance properties and qualities. In some aspects, as disclosed herein, the polymer compositions comprise a building block comprising various 2,2-bisimidazoles. In such aspects, the 2,2'-bisimidazoles can be used to build a large variety of polymers having a wide range of functional groups. In still further aspects, the polymers comprising the 2,2'-bisimidazole building block can be further modified post-polymerization.

In certain aspects, disclosed herein is a polymer composition comprising a repeating unit of formula (I):

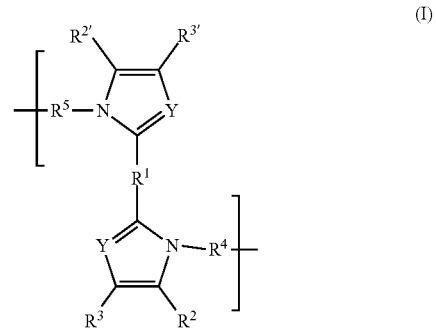

wherein,
$R^1$ is selected from null, $C_1$-$C_{10}$ alkyl, $C_1$-$C_{10}$ perfluoroalkyl, $C_6$-$C_{14}$ aryl, or $C_1$-$C_{13}$ heteroaryl;
$R^2$, $R^{2'}$, $R^3$, and $R^{3'}$ are, each independent of the other, selected from hydrogen, $C_1$-$C_{10}$ alkyl, $C_1$-$C_{10}$ alkoxy, $C_6$-$C_{14}$ aryl, $C_1$-$C_{13}$ heteroaryl, $C_6$-$C_{14}$ aryloxy, wherein each of $R^2$, $R^{2'}$, $R^3$, or $R^{3'}$ independent of the other, is optionally substituted with $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, amino, carbonyl, ester, ether, halide, carboxyl, hydroxy, nitro, cyano, silyl, sulfo-oxo, sulfonyl, sulfone, sulfoxide, thiol, or phosphonyl; or wherein $R^2$ and $R^3$ together form a 6 membered ring containing 6 carbon atoms; and/or wherein $R^{2'}$ and $R^{3'}$ together form a 6 membered ring containing 6 carbon atoms; and wherein $R^2$ and $R^{2'}$ are the same or different; wherein $R^3$ and $R^{3'}$ are the same or different;

$R^4$ and $R^5$ are, independently, $[R^A\text{—}R^B\text{—}R^C]_m$, wherein, wherein: $R^A$, $R^B$, and $R^C$, each independent of the other, selected from null, carboxyl group, hydroxy group, $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, $C_6$-$C_{14}$ aryloxy, $C_3$-$C_{10}$ cycloalkyl, or $C_3$-$C_{10}$ cycloalkenyl, heterocycloalkyl, imide, cyclic imide, imidazole, polyester, polysulfone, poly(aryl ether ketone), and wherein $R^A$, $R^B$, and $R^C$, are each independently of each other optionally substituted with $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, carbonyl, ester, ether, halide, carboxyl, hydroxy, nitro, cyano, silyl, sulfo-oxo, sulfonyl, sulfone, sulfoxide, thiol, or phosphonyl;

wherein any of $R^A$, $R^B$, or $R^C$ are the same or different; and wherein at least one of $R^A$, $R^B$, and $R^C$ is not null; and Y is N or $N^+$—$R^6$, wherein:
$R^6$ is selected from hydrogen, $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, or $C_6$-$C_{14}$ aryloxy, wherein $R^6$, is optionally, substituted with $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, carbonyl, ester, ether, halide, carboxyl, hydroxy, nitro, cyano, silyl, sulfo-oxo, sulfonyl, sulfone, sulfoxide, thiol, or phosphonyl.

Still further disclosed herein are aspects wherein when Y is $N^+$—$R^6$, the composition further comprises a counter anion X, wherein X is selected from chloride, bromide, iodide, nitrate, dicyanamide, acetate, bis(trifluoromethane) sulfonimide, hexafluorophosphate, tetrafluoroborate, sulfate, phosphate, tris(perfluoroalkyl)trifluorophosphatemesylate, thiocyanide, mesylate, triflate, or tosylate. In still further exemplary aspects, when Y is $N^+$—$R^6$, the composition comprises an ionic liquid.

In still further aspects, it is understood that $R^4$ and $R^5$ independently can comprise $[R^A\text{—}R^B\text{—}R^C\text{—}R^D\text{—}R^E\text{—}\ldots]_m$. In other words, it is understood that $R^4$ and $R^5$, independently, can comprise more than repeating units of three components $R^A\text{—}R^B\text{—}R^C$, it can also comprise repeating units of four components, such as $R^A\text{—}R^B\text{—}R^C\text{—}R^D$, or five components $R^A\text{—}R^B\text{—}R^C\text{—}R^D\text{—}R^E$, or beyond. In such aspects, each of $R^D$ or $R^E$ or any additional component can be selected from null, carboxyl group, hydroxy group, $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, $C_6$-$C_{14}$ aryloxy, $C_3$-$C_{10}$ cycloalkyl, or $C_3$-$C_{10}$ cycloalkenyl, heterocycloalkyl, imide, cyclic imide, imidazole, polyester, polysulfone, poly(aryl ether ketone), and wherein $R^D$, $R^E$, or any additional component, are each independently of each other optionally substituted with $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, carbonyl, ester, ether, halide, carboxyl, hydroxy, nitro, cyano, silyl, sulfo-oxo, sulfonyl, sulfone, sulfoxide, thiol, or phosphonyl. In still further aspects, also $R^D$, $R^E$, or any additional component can be the same or different. It also is the same or different as $R^A$, $R^B$, or $R^C$. Yet in still further aspects, at least one of $R^A$, $R^B$, $R^C$, $R^D$, $R^E$, or any additional component is not null; and wherein m can be an integer from 1 to 100.

In still further aspects, the disclosed polymer compositions can comprise homopolymers, graft polymers, or block polymers. In yet further aspects, the polymer compositions disclosed herein can comprise random copolymers. In yet other aspects, the polymers disclosed herein can comprise alternating copolymers. It is understood that in some aspects, the polymer is a homopolymer. While in other aspects, the polymer is a graft polymer or a block polymer. It is understood that in exemplary aspects, wherein the polymer is a block polymer, the polymer can comprise any known in the art block polymer configurations. For example, and without limitation, in some aspects, the polymers disclosed herein can comprise diblock polymers (AB), or triblock polymers (ABA or ABC), or tetrablock terpolymers of ABCA type. It is understood that in such exemplary aspects, the letters A, B, and C, represent an individual polymer block present in the block copolymer.

In still further aspects, the compositions disclosed herein is a polymerization product of one or more monomers, wherein at least one monomer has a general formula (II):

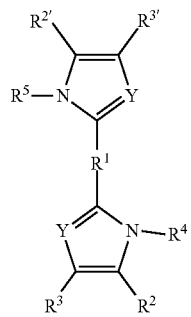

wherein,
$R^1$ is selected from null, $C_1$-$C_{10}$ alkyl, $C_1$-$C_{10}$ perfluoroalkyl, $C_6$-$C_{14}$ aryl, or $C_1$-$C_{13}$ heteroaryl;
$R^2$, $R^{2'}$, $R^3$, and $R^{3'}$ are, each independent of the other, selected from are, each independent of the other, selected from hydrogen, $C_1$-$C_{10}$ alkyl, $C_1$-$C_{10}$ alkoxy, $C_6$-$C_{14}$ aryl, $C_1$-$C_{13}$ heteroaryl, or $C_6$-$C_{14}$ aryloxy, wherein each of $R^2$, $R^{2'}$, $R^3$, or $R^{3'}$ independent of the other, is optionally substituted with $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, amino, carbonyl, ester, ether, halide, carboxyl, hydroxy, nitro, cyano, silyl, sulfo-oxo, sulfonyl, sulfone, sulfoxide, thiol, or phosphonyl; or wherein
$R^2$ and $R^3$ together form a 6 membered ring containing 6 carbon atoms; and/or wherein
$R^{2'}$ and $R^{3'}$ together form a 6 membered ring containing 6 carbon atoms; and wherein
$R^2$ and $R^{2'}$ are the same or different; wherein
$R^3$ and $R^{3'}$ are the same or different;
$R^4$ and $R^5$ are independently $[R^{A'}\text{—}R^{B'}\text{—}R^{C'}]_m$, wherein: $R^{A'}$, $R^{B'}$, and $R^{C'}$, each independent of the other selected from null, hydrogen, hydroxy group, an amino group, $C_1$-$C_{10}$ alkyl, $C_1$-$C_{10}$ alkoxy, carboxyl group, $C_2$-$C_{10}$ alkenyl, $C_2$-$C_{10}$ alkynyl, $C_6$-$C_{14}$ aryl, $C_1$-$C_{13}$ heteroaryl, $C_6$-$C_{14}$ aryloxy, $C_3$-$C_{10}$ cycloalkyl, or $C_3$-$C_{10}$ cycloalkenyl, imide, cyclic imide, imidazole, polyester, polysulfone, poly(aryl ether ketone), and wherein $R^{A'}$, $R^{B'}$, and $R^{C'}$, are each independently of each other optionally substituted with $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, carbonyl, ester, ether, halide, carboxyl, hydroxy, nitro, cyano, silyl, sulfo-oxo, sulfonyl, sulfone, sulfoxide, thiol, or phosphonyl; wherein at least one of $R^{A'}$, $R^{B'}$, and $R^{C'}$ is not null, wherein any of $R^{A'}$, $R^{B'}$ or $R^{C'}$ the same or different; wherein at least one of $R^{A'}$, $R^{B'}$, and $R^{C'}$ is not null; and wherein m is an integer from 1 to 100; and Y is N or $N^+$—$R^6$, wherein $R^6$ is selected from hydrogen, $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, or $C_6$-$C_{14}$ aryloxy, wherein $R^6$ is optionally substituted with $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, imide, cyclic imide, imidazole, imidazolium cation, carbonyl, ester, ether, halide, carboxyl, hydroxy, nitro, cyano, silyl, sulfo-oxo, sulfonyl, sulfone, sulfoxide, thiol, or phosphonyl.

Again, as disclosed above, the representation of $R^4$ and $R^5$ as $[R^{A'}$—$R^{B'}$—$R^{C'}]_m$ is exemplary, and it can also be represented by $[R^{A'}$—$R^{B'}$—$R^{C'}$—$R^{D'}$—$R^{E'}$— ... ]$_m$. In other words, it is understood that in such exemplary aspect, $R^4$ and $R^5$, independently, can comprise more than repeating units of three components $R^{A'}$—$R^{B'}$—$R^{C'}$, it can also comprise repeating units of four components, such as $R^{A'}$—$R^{B'}$—$R^{C'}$—$R^{D'}$, or five components $R^{A'}$—$R^{B'}$—$R^{C'}$—$R^{D'}$—$R^{E'}$, or beyond. In such aspects, each of $R^{D'}$ or $R^{E'}$ or any additional component can be selected from null, carboxyl group, hydroxy group, $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, $C_6$-$C_{14}$ aryloxy, $C_3$-$C_{10}$ cycloalkyl, or $C_3$-$C_{10}$ cycloalkenyl, heterocycloalkyl, imide, cyclic imide, imidazole, polyester, polysulfone, poly(aryl ether ketone), and wherein $R^{D'}$, $R^{E'}$, or any additional component, are each independently of each other optionally substituted with $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, carbonyl, ester, ether, halide, carboxyl, hydroxy, nitro, cyano, silyl, sulfo-oxo, sulfonyl, sulfone, sulfoxide, thiol, or phosphonyl. In still further aspects, also $R^{D'}$, $R^{E'}$, or any additional component can be the same or different. It can also be the same or different as $R^{A'}$, $R^{B'}$, or $R^{C'}$. Yet in still further aspects, at least one of $R^{A'}$, $R^{B'}$, $R^{C'}$, $R^{D'}$, $R^{E'}$, or any additional component is not null, and wherein m can be an integer from 1 to 100.

In yet further aspects, the at least one monomer can be selected from

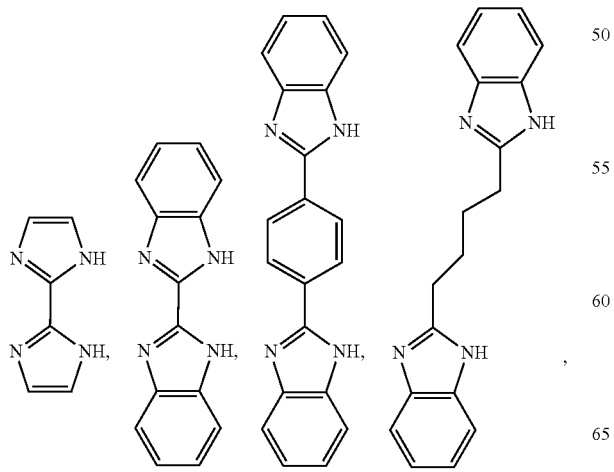

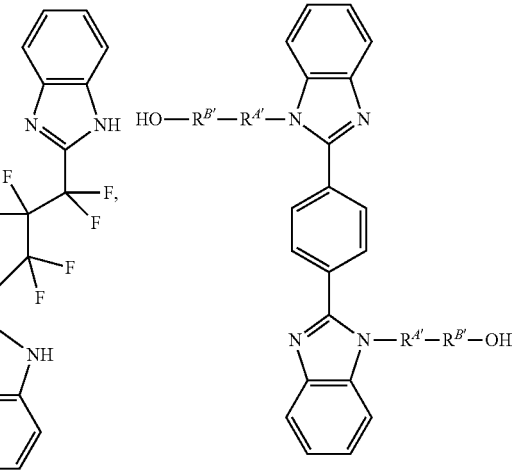

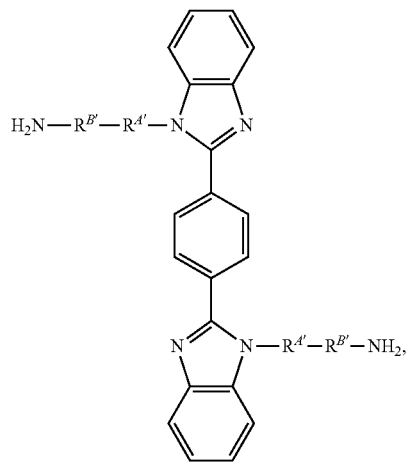

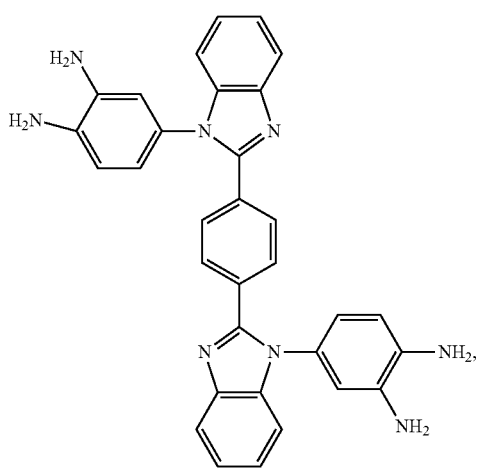

29
-continued

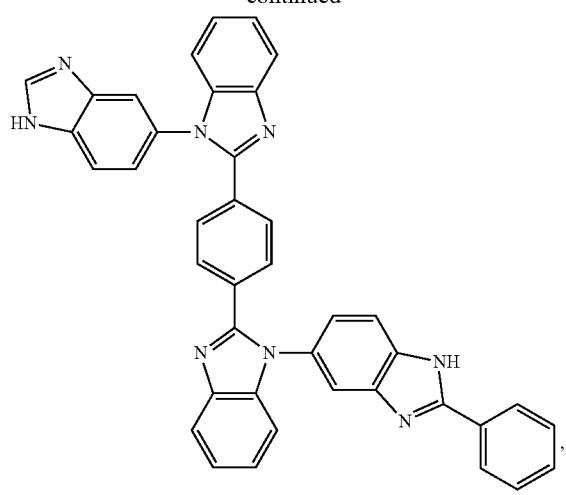

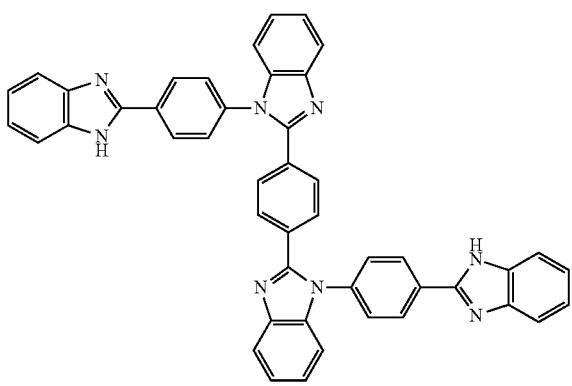

30
-continued

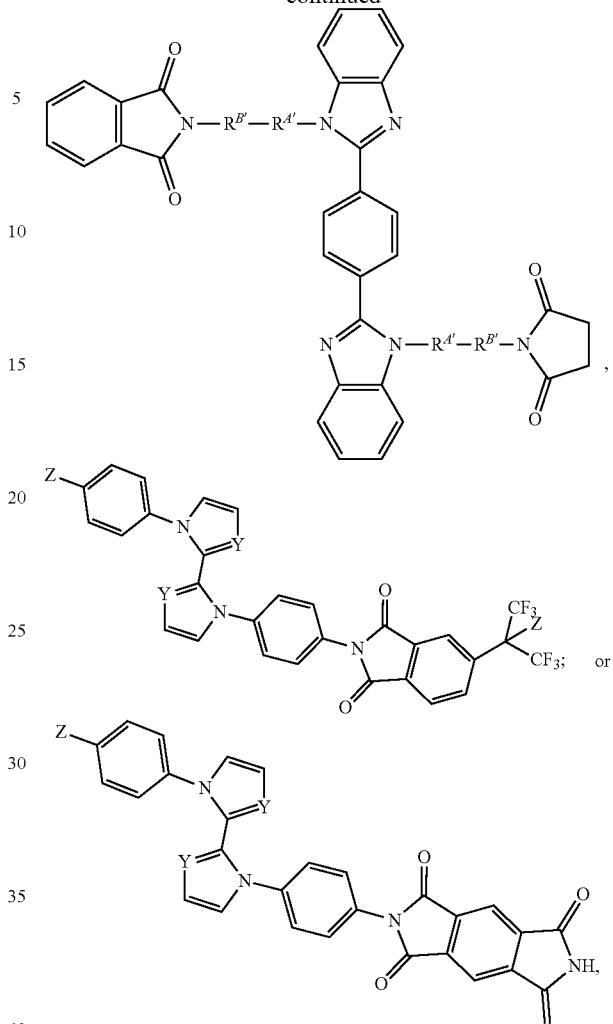

wherein
$R^{A'}$ and $R^{B'}$, each independent of the other selected from null, carboxyl group, hydroxy group, $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, $C_6$-$C_{14}$ aryloxy, $C_3$-$C_{10}$ cycloalkyl, or $C_3$-$C_{10}$ cycloalkenyl, imide, cyclic imide, imidazole, polyester, polysulfone, poly(aryl ether ketone), and wherein $R^{A'}$ and $R^{B'}$, are each independently of each other optionally substituted with $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, carbonyl, ester, ether, halide, carboxyl, hydroxy, nitro, cyano, silyl, sulfo-oxo, sulfonyl, sulfone, sulfoxide, thiol, or phosphonyl; and wherein at least one of $R^{A'}$ and $R^{B'}$ is not null, and wherein $R^A$ and $R^{A'}$ and $R^B$ and $R^{B'}$ are the same; and wherein Z is selected from hydrogen, OH, or $NH_2$; Y is N or $N^+$—$R^6$, wherein $R^6$ is selected from hydrogen, $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, or $C_6$-$C_{14}$ aryloxy, wherein $R^6$ is optionally substituted with $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, imide, cyclic imide, imidazole, imidazolium cation, carbonyl, ester, ether, halide, carboxyl, hydroxy, nitro, cyano, silyl, sulfo-oxo, sulfonyl, sulfone, sulfoxide, thiol, or phosphonyl.

It is understood, however, that Z can be selected from any appropriate nucleophile. For example, and without limitations, Z can be selected from —SH, —COOH, halogen, or cyanide groups. It is also understood that Z does not have to be a primary amine, it can be a secondary or tertiary amine if desired.

It is understood that monomer units, as disclosed herein, can be modified or functionalized to obtain the compositions exhibiting the desired thermal, conductive, and/or mechanical properties.

In yet further exemplary and unlimiting aspects, the at least one monomer is selected from 2,2-biimidazole, 2,2-bibenzimidazole, 2,2'-(1,4-phenylene) bis(benzimidazole) or 2,2'-(1,4-butanediyl)bis(benzimidazole) or 2,2'-(perfluorobutane-1,4-diyl)bis(1H-benzo[d]imidazole):

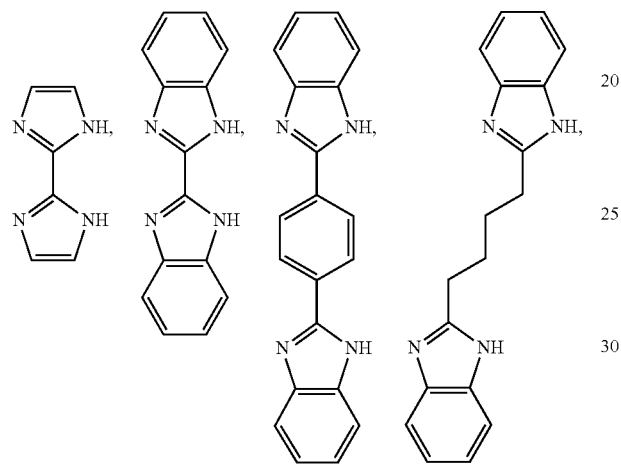

In still further aspects, the at least one monomer disclosed herein can be further polymerized or functionalized to form the polymer compositions comprising:

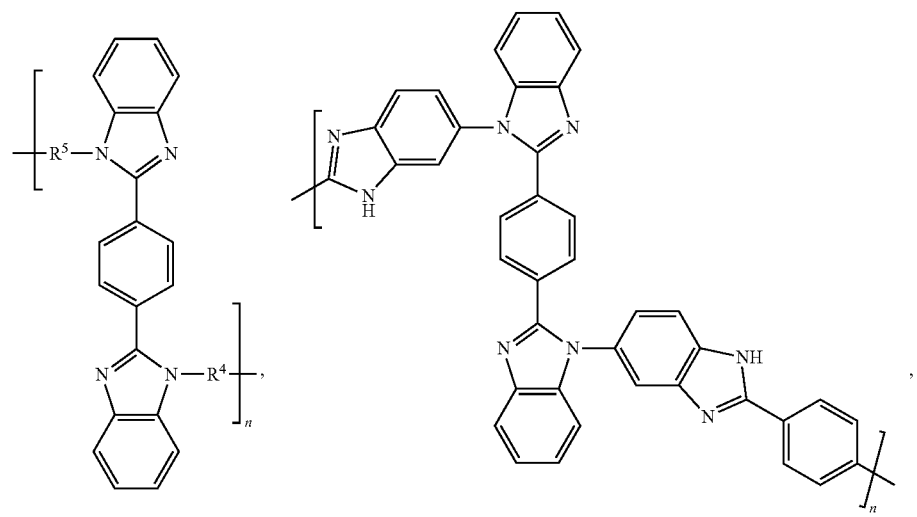

-continued
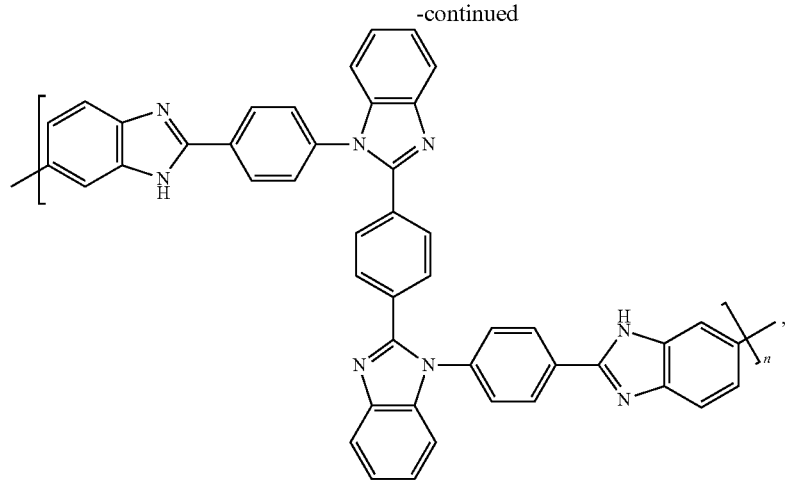
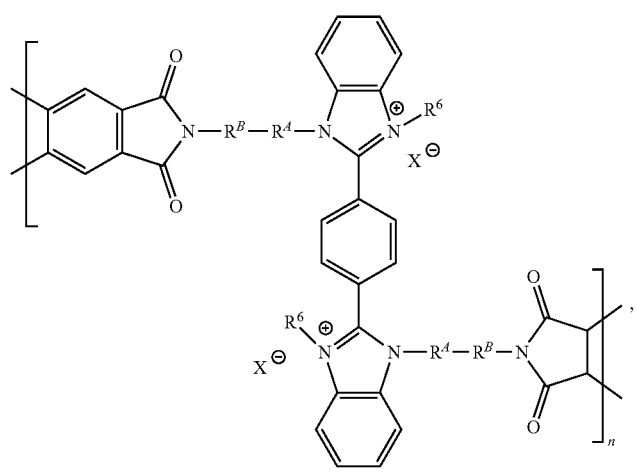
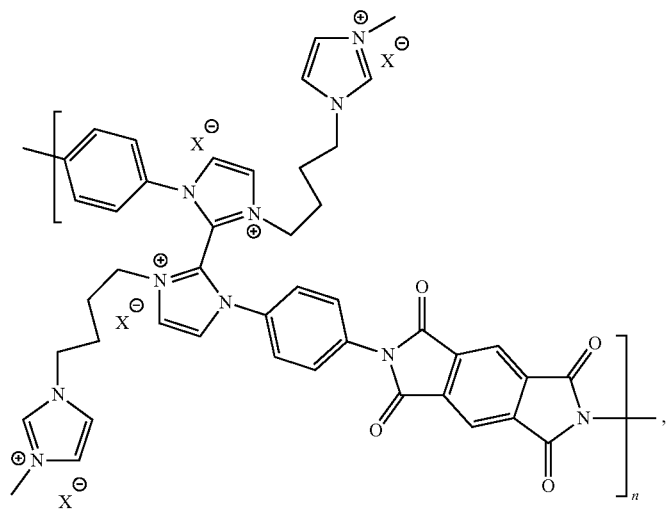

-continued

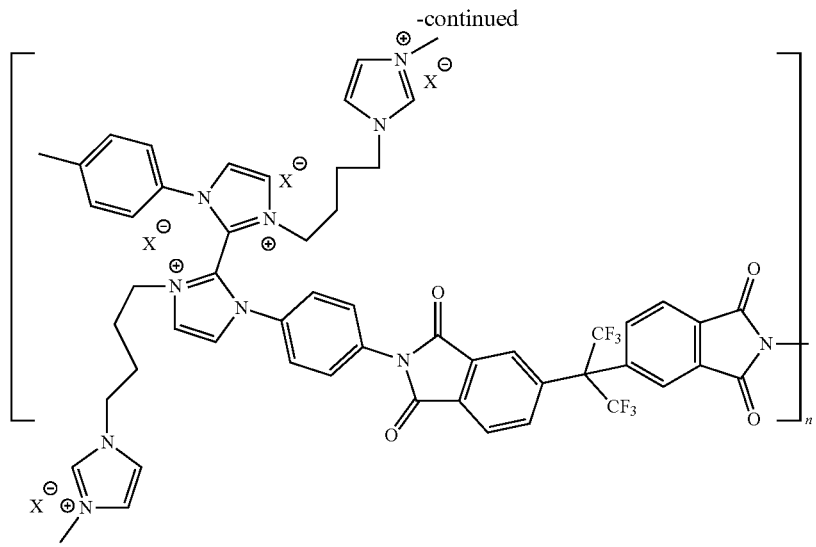

wherein $R^4$ and $R^5$ are, independently, $[R^{A'}—R^{B'}—R^{C'}]_m$, wherein:

$R^{A'}$, $R^{B'}$, $R^{C'}$, $R^A$, and $R^B$ each independent of the other selected from null, carboxyl group, hydroxy group, $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, $C_6$-$C_{14}$ aryloxy, $C_3$-$C_{10}$ cycloalkyl, or $C_3$-$C_{10}$ cycloalkenyl, heterocycloalkyl, polyester, imide, cyclic imide, imidazole, polysulfone, poly(aryl ether ketone), and wherein $R^A$, $R^B$, and $R^C$, are each independently of each other optionally substituted with $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, carbonyl, ester, ether, halide, carboxyl, hydroxy, nitro, cyano, silyl, sulfo-oxo, sulfonyl, sulfone, sulfoxide, thiol, or phosphonyl; and wherein any of $R^{A'}$, $R^{B'}$ or $R^{C'}$ are optionally the same; and wherein at least one of $R^{A'}$, $R^{B'}$, and $R^{C'}$ is not null; or wherein at least one of $R^A$ or $R^B$ is not null, wherein m is an integer from 1 to 100, and wherein n is an integer from 1 to 100,000.

In yet further aspects, m can have integer value in the disclosed range, including exemplary values of 2, 5, 10, 20, 30, 40, 50, 60, 70, 80, and 90. It is understood that m can have any values between any two foregoing values, for example, m can be from 1 to 20 or from 20 to 50 or from 50 to 100. In yet further aspects, n can have integer value in the disclosed range, including exemplary values of 2, 5, 10, 100, 500, 1,000, 5,000, 10,000, 50,000, 80,000, and 90,000. It is understood that n can have any values between any two foregoing values, for example, n can be from 1 to 10 or from 10 to 5,000 or from 50 to 50,000, etc.

In still further aspects, the compositions disclosed herein are configured to substantially withstand temperature in a range from about 100° C. to about 600° C., including exemplary values of about 200° C., about 250° C., about 300° C., about 350° C., about 400° C., about 450° C., about 500° C., and about 550° C. In still further aspects, the compositions disclosed herein substantially withstand temperature in a range from about 100° C. to about 600° C.

In yet further aspects, the compositions disclosed herein are substantially flame resistant. It is understood that the compositions disclosed herein are able to withstand fire or give protection from it for a period of time.

In still further aspects, the compositions disclosed herein can exhibit various properties. In certain aspects, the composition can exhibit adhesive properties, antifungal properties, catalytic properties, antistatic properties, or any combination thereof. It is understood that in certain aspects, the compositions disclosed herein can be used as a catalyst. In still further aspects, the compositions described herein can be used as adhesives. In still further aspects, the compositions can exhibit antifungal properties. While in other aspects, the compositions can exhibit antistatic properties.

In still further aspects, various articles can be manufactured from the disclosed compositions. In such exemplary aspects, disclosed herein are articles comprising the disclosed compositions. In certain aspects, the compositions can be used as a starting material for 3-D printing. In still further aspects, disclosed herein are 3-D printing materials comprising compositions as disclosed herein. In yet further aspects, the articles comprising the disclosed compositions can comprise any articles that can be prepared from the polymer compositions. Due to exceptional chemical and wear resistance properties of the compositions, the articles can comprise components for daily use, military use, high temperature use, medical use, electronics, mining, space industry, textile, first responders clothing and equipment, etc. In yet further aspects, the articles can comprise fabrics, gloves, cords, tapes, membranes, sensors, tubing, sheets of materials, blocks of materials, or any combination thereof. In certain aspects, the compositions disclosed herein can be used as gas separation membranes. In yet other aspects, the compositions disclosed herein can be used as fuel cell membranes.

Methods

Also disclosed herein are various methods. In some aspects, disclosed herein are methods for making the inventive compositions. In yet further aspects, disclosed herein is a method comprising: a condensation polymerization of reactants, wherein the reactants comprise one or more monomers and wherein at least one monomer has a general formula (II)

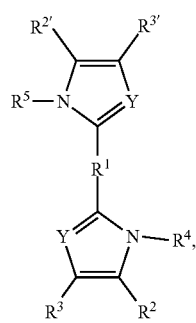

(II)

wherein
  R$^1$ is selected from null, C$_1$-C$_{10}$ alkyl, C$_1$-C$_{10}$ perfluoroalkyl, C$_6$-C$_{14}$ aryl, or C$_1$-C$_{13}$ heteroaryl;
  R$^2$, R$^{2'}$, R$^3$, and R$^{3'}$ are, each independent of the other, selected from hydrogen, C$_1$-C$_{10}$ alkyl, C$_1$-C$_{10}$ alkoxy, C$_6$-C$_{14}$ aryl, C$_1$-C$_{13}$ heteroaryl, or C$_6$-C$_{14}$ aryloxy, wherein each of R$^2$, R$^{2'}$, R$^3$, or R$^{3'}$ independent of the other, is optionally substituted with C$_1$-C$_{10}$ alkyl, C$_1$-C$_{10}$ alkoxy, C$_2$-C$_{10}$ alkenyl, C$_2$-C$_{10}$ alkynyl, C$_6$-C$_{14}$ aryl, C$_1$-C$_{13}$ heteroaryl, amino, carbonyl, ester, ether, halide, carboxyl, hydroxy, nitro, cyano, silyl, sulfo-oxo, sulfonyl, sulfone, sulfoxide, thiol, or phosphonyl; or
  wherein R$^2$ and R$^3$ together form a 6 membered ring containing 6 carbon atoms; and/or
  wherein R$^{2'}$ and R$^{3'}$ together form a 6 membered ring containing 6 carbon atoms;
  wherein R$^2$ and R$^{2'}$ are the same or different;
  wherein R$^3$ and R$^{3'}$ are the same or different;
  R$^4$ and R$^5$ are independently [R$^{A'}$—R$^{B'}$—R$^{C'}$]$_m$, wherein: R$^{A'}$, R$^{B'}$, and R$^{C'}$, each independent of the other selected from null, hydrogen, hydroxy group, an amino group, C$_1$-C$_{10}$ alkyl, C$_1$-C$_{10}$ alkoxy, carboxyl group, C$_2$-C$_{10}$ alkenyl, C$_2$-C$_{10}$ alkynyl, C$_6$-C$_{14}$ aryl, C$_1$-C$_{13}$ heteroaryl, C$_6$-C$_{14}$ aryloxy, C$_3$-C$_{10}$ cycloalkyl, heterocycloalkyl, or C$_3$-C$_{10}$ cycloalkenyl, imide, cyclic imide, imidazole, polyester, polysulfone, poly(aryl ether ketone), and wherein R$^{A'}$, R$^{B'}$, and R$^{C'}$, are each independently of each other optionally substituted with C$_1$-C$_{10}$ alkyl, C$_1$-C$_{10}$ alkoxy, C$_2$-C$_{10}$ alkenyl, C$_2$-C$_{10}$ alkynyl, C$_6$-C$_{14}$ aryl, C$_1$-C$_{13}$ heteroaryl, carbonyl, ester, ether, halide, carboxyl, hydroxy, nitro, cyano, silyl, sulfo-oxo, sulfonyl, sulfone, sulfoxide, thiol, or phosphonyl; wherein any of R$^{A'}$, R$^{B'}$ or R$^{C'}$ are optionally the same, and wherein m is an integer from 1 to 100; Y is N or N$^+$—R$^6$, wherein R$^6$ is selected from hydrogen, C$_1$-C$_{10}$ alkyl, C$_1$-C$_{10}$ alkoxy, C$_2$-C$_{10}$ alkenyl, C$_2$-C$_{10}$ alkynyl, C$_6$-C$_{14}$ aryl, C$_1$-C$_{13}$ heteroaryl, or C$_6$-C$_{14}$ aryloxy, wherein R$^6$ is optionally substituted with C$_1$-C$_{10}$ alkyl, C$_1$-C$_{10}$ alkoxy, C$_2$-C$_{10}$ alkenyl, C$_2$-C$_{10}$ alkynyl, C$_6$-C$_{14}$ aryl, C$_1$-C$_{13}$ heteroaryl, imide, cyclic imide, imidazole, imidazolium cation, carbonyl, ester, ether, halide, carboxyl, hydroxy, nitro, cyano, silyl, sulfo-oxo, sulfonyl, sulfone, sulfoxide, thiol, or phosphonyl.

In yet further aspects, at least one of R$^{A'}$, R$^{B'}$, and R$^{C'}$ is not null.

In yet further aspects, R$^2$, R$^{2'}$, R$^3$, and R$^{3'}$ are, each independent of the other is hydrogen; or R$^2$ and R$^3$ together form a 6 membered ring containing 6 carbon atoms; and/or R$^{2'}$ and R$^{3'}$ together form a 6 membered ring containing 6 carbon atoms; and wherein R$^2$ and R$^{2'}$ are the same or different; wherein R$^3$ and R$^{3'}$ are the same or different; R$^4$ and R$^5$ are independently [R$^{A'}$—R$^{B'}$—R$^{C'}$]$_m$, wherein: at least one of R$^{A'}$ or R$^{B'}$ is not null and wherein R$^{C'}$ is an amino, hydroxy, carboxyl group, or heteroaryl group.

In still further aspects, the disclosed herein methods comprise any of the described above monomers.

In certain aspects, the monomers can be polymerized directly via an alkylating reaction, as shown in Eq. 1, for example:

(Eq. 1)

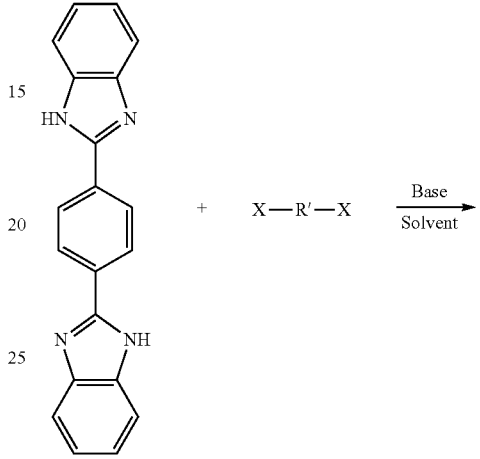

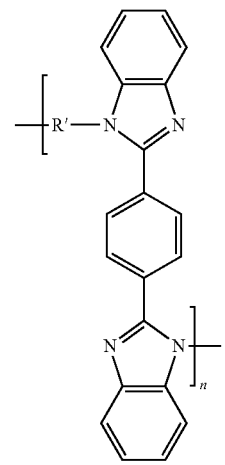

In certain aspects, R' can be selected from C$_1$-C$_{10}$ alkyl, C$_1$-C$_{10}$ alkoxy, C$_6$-C$_{14}$ aryl, C$_1$-C$_{13}$ heteroaryl, C$_6$-C$_{14}$ aryloxy, C$_3$-C$_{10}$ cycloalkyl, or C$_3$-C$_{10}$ cycloalkenyl, polyester, polysulfone, poly(aryl ether ketone). In yet other aspects, R' can also be optionally substituted with C$_1$-C$_{10}$ alkyl, C$_1$-C$_{10}$ alkoxy, C$_2$-C$_{10}$ alkenyl, C$_2$-C$_{10}$ alkynyl, C$_6$-C$_{14}$ aryl, C$_1$-C$_{13}$ heteroaryl, carbonyl, ester, ether, halide, carboxyl, hydroxy, nitro, cyano, silyl, sulfo-oxo, sulfonyl, sulfone, sulfoxide, thiol, or phosphonyl. In still further aspects, X can be Cl, Br, I, O, O-Ph-SO$_3$CH$_3$, SO$_3$CH$_3$, or SO$_3$CH$_3$.

In yet other exemplary aspects, the suitable alkylating agents that can be used in the disclosed methods are represented by X—R'—X, wherein R' can be substituted or unsubstituted C$_{1-20}$ alkyl, substituted or unsubstituted C$_{2-20}$ alkenyl, substituted or unsubstituted C$_{2-20}$ alkynyl, substituted or unsubstituted C$_{1-20}$ heteroalkyl, substituted or unsubstituted C$_{2-20}$ heteroalkenyl, substituted or unsubstituted C$_{2-20}$ heteroalkynyl, substituted or unsubstituted cycloalkyl, substituted or unsubstituted heterocycloalkyl, substituted or unsubstituted aryl, substituted or unsubstituted heteroaryl, or mixtures thereof, wherein any of the substituted groups named can be substituted with one or more of alkyl, halogen, alkoxyl, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol groups; and wherein X is Cl, Br, I, O, O-Ph-SO$_3$CH$_3$, SO$_3$CH$_3$, or SO$_3$CH$_3$.

Possible examples of suitable alkylating agents are shown in the scheme below. In some aspects, the alkylating agent comprises at least two leaving groups. Some leaving groups include, but are not limited to, chlorine, bromine, iodine, methanesulfonyl (mesylate), trifluoromethanesulfonyl (triflate), or p-toluenesulfonyl (tosylate). A substitution reaction can take place between the alkylating agent and the heteroaryl as described above. A suitable bridge can connect the two leaving groups. The bridge can be selected based on its impact on the chemical or physical properties of the resulting polymer. The bridge can comprise alkyl, alkenyl, alkynyl, aryl, ether, or ester functionality. Some examples of suitable bridges are also shown below:

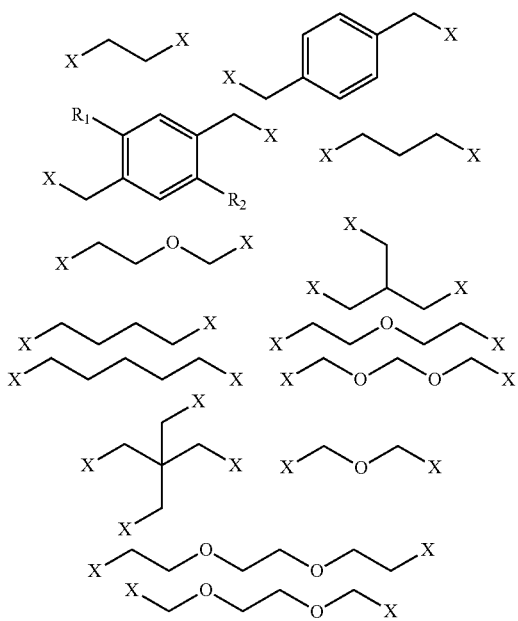

In yet further aspects, the leaving groups can be used as an anion for the cationic monomer as a byproduct of the reaction between the alkylating agent and the bridging monomer. In some aspects, the anion can be exchanged for another anion that can improve properties, such as viscosity, CO$_2$ affinity, or melting point. The anion can be exchanged by methods known to a person skilled in the art.

Some suitable anions that can be utilized are shown below. In some aspects, the anion can be chloride, bromide, iodide, nitrate, dicyanamide, acetate, bis(trifluoromethane)sulfonamide, hexafluorophosphate, tetrafluoroborate, sulfate, phosphate, tris(perfluoroalkyl)trifluorophosphatemesylate, aluminum chloride, thiocyanide, mesylate, triflate, or tosylate.

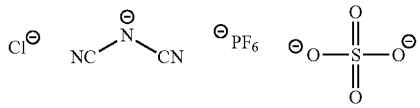

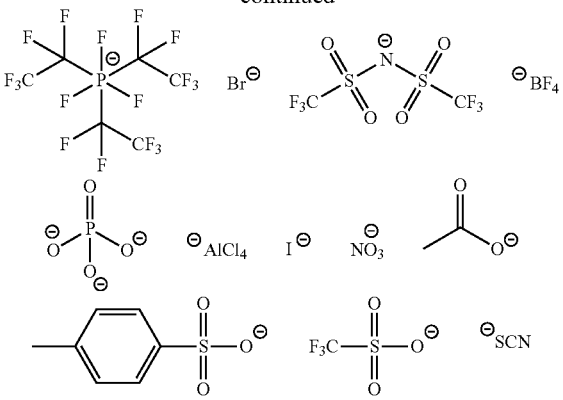

In still further aspects, n can be any integer from 1 to 100,000. In yet further aspects, n can have integer value in the disclosed range, including exemplary values of 2, 5, 10, 100, 500, 1,000, 5,000, 10,000, 50,000, 80,000, or 90,000. It is understood that n can have any values between any two foregoing values, for example, n can be from 1 to 10 or from 10 to 5,000 or from 50 to 50,000, etc.

It is understood that any known in the art mild bases and solvents can be used to form the polymer according to Eq. 1. In certain aspects, the bases used herein can comprise metal carbonates (e.g., K$_2$CO$_3$), metal hydroxides (e.g., NaOH), ammonium hydroxides (e.g., tetramethylammonium hydroxide), metal hydrides (e.g., NaH), or any combinations thereof. In yet other aspects, the solvents can comprise tetrahydrofuran, acetone, methyl ethyl ketone, acetonitrile, N, N-dimethylformamide, or dimethyl sulfoxide, or any combination thereof.

The reaction can also be optionally heated up to about 150° C., or up to about 140° C., or up to about 130° C., or up to about 120° C., or up to about 110° C., or up to about 100° C. The reaction mixture can be stirred and heated for up to 48 hours to generate the monomer. The monomer can be isolated by any known in the art methods.

In yet further aspects, the at least one monomer as disclosed herein can be functionalized, such that it becomes amenable to the formation of other types of polymers with —NH$_2$ or —OH groups according to Eq. 2:

(Eq. 2)

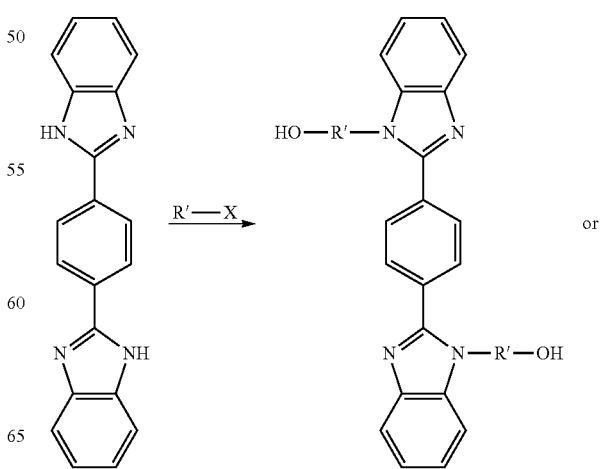

or

-continued

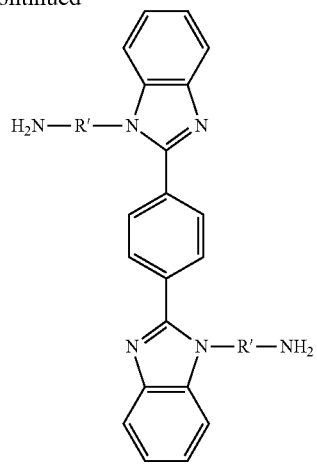

In still further aspects, R' can be selected from $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, $C_6$-$C_{14}$ aryloxy, $C_3$-$C_{10}$ cycloalkyl, or $C_3$-$C_{10}$ cycloalkenyl, polyester, polysulfone, poly(aryl ether ketone). In yet other aspects, R' can also be optionally substituted with $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, carbonyl, ester, ether, halide, carboxyl, hydroxy, nitro, cyano, silyl, sulfo-oxo, sulfonyl, sulfone, sulfoxide, thiol, or phosphonyl. In some exemplary aspects, R' can be any alkyl, ether, or aryl. In still further aspects, X can be Cl, Br, I, O, O-Ph-$SO_3CH_3$, $SO_3CH_3$, or $SO_3CH_3$.

In still further aspects, any of the above-formed polymers can also serve as monomers to former disclosed herein compositions. In certain exemplary aspects, the hydroxyl-terminated monomers, as shown in Eq. 2, can be used for the synthesis of polyester, polysulfones, poly(aryl ether ketones), or any combination thereof. While in other exemplary aspects, the amine-terminated monomers (Eq.2) can be used to synthesize polyamides, polyimides, polyacrylamides, or any combinations thereof. It is further understood that R' groups, as shown in Eq. 1 and 2, can be any of the R groups disclosed herein.

It is understood that the functional (or terminal) groups, as shown in Eq. 2, are not limited to hydroxyl or amine groups and can also comprise carboxylic acids and halides, for example. It is further understood that the specific properties of the final composition can be affected by a specific R' group. For example, and without limitations, polymers with R' group selected from aryl based functional groups can provide for a robust polymer composition. In yet further aspects, the robust polymer composition, as described herein, refers to a composition exhibiting thermal stability at temperatures of greater than about 450° C., greater than about 500° C., greater than about 550° C., or about 600° C. In yet further aspects, the robust compositions described herein are capable of substantially withstanding temperatures from greater than 450° C. to about 600° C. without a substantial mass loss.

Yet, in further aspects, the disclosed herein polymers can be formed according to Eq. 3.

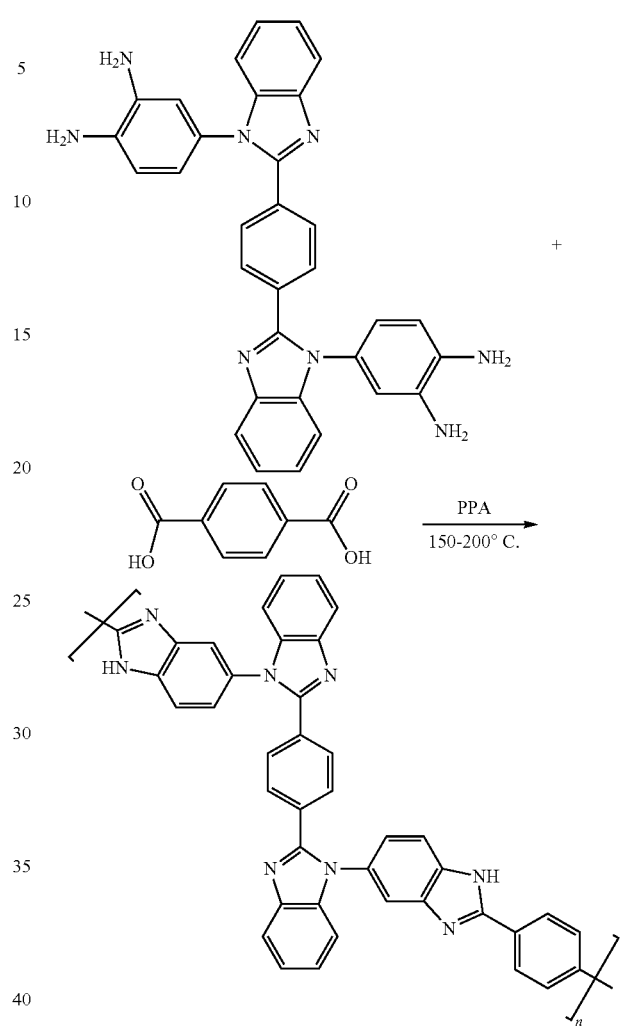

(Eq. 3)

In still further aspects, various catalysts can be used to catalyze the polymerization reaction. In certain aspects, it is understood that any catalysts useful for the polymerization reactions can be utilized. In certain exemplary aspects, catalysts such as polyphosphoric acid (PPA) can be used as a catalyst. In yet other aspects, the polyphosphoric acid can also be used as a solvent. However, it is understood that the polyphosphoric acid is only exemplary and non-limiting, and any catalysts having similar properties can be utilized. It is further understood that the catalysts that can be used to form the disclosed compositions can be supported and/or unsupported.

In yet further aspects, the reaction can also be heated up to a temperature between about 150° C. to about 200° C., including exemplary values of about 160° C., about 170° C., about 180° C., and about 190° C.

Again and as described above, n can be an integer from 1 to 100,000. In yet further aspects, n can have integer value in the disclosed range, including exemplary values of 2, 5, 10, 100, 500, 1,000, 5,000, 10,000, 50,000, 80,000, or 90,000. It is understood that n can have any values between any two foregoing values, for example, n can be from 1 to 10 or from 10 to 5,000 or from 50 to 50,000, etc.

In yet other exemplary aspects, the disclosed herein polymers can be formed according to Eq. 4

(Eq. 4)

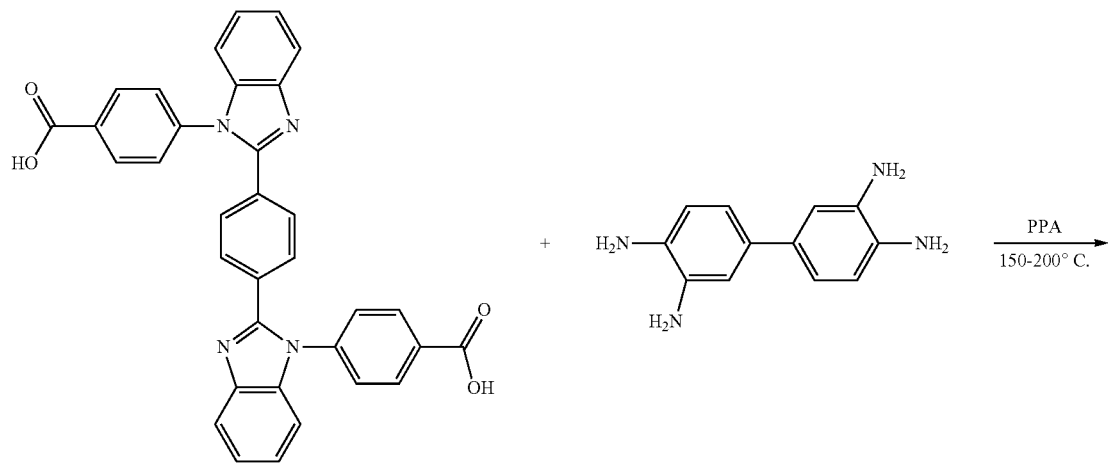

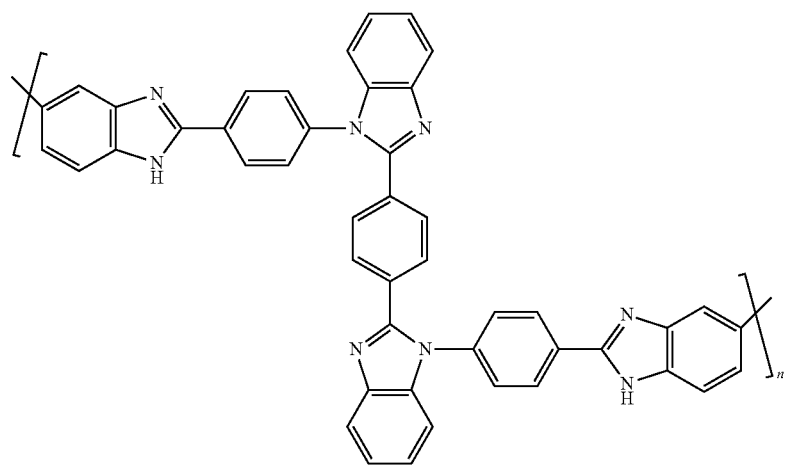

Similarly, in these exemplary aspects, n is an integer from 1 to 100,000. In yet further aspects, n can have integer value in the disclosed range, including exemplary values of 2, 5, 10, 100, 500, 1,000, 5,000, 10,000, 50,000, 80,000, or 90,000. It is understood that n can have any values between any two foregoing values, for example, n can be from 1 to 10 or from 10 to 5,000 or from 50 to 50,000, etc.

In still further aspects, the polymers formed by the methods disclosed herein can be alkylated to form, for example, and without limitation benzimidazolium salt as shown in Eq. 5. In such exemplary aspects, the polymer can also interact with ionic liquids. In yet further aspects, the methods disclosed herein comprise adding an ionic liquid.

(Eq. 5)

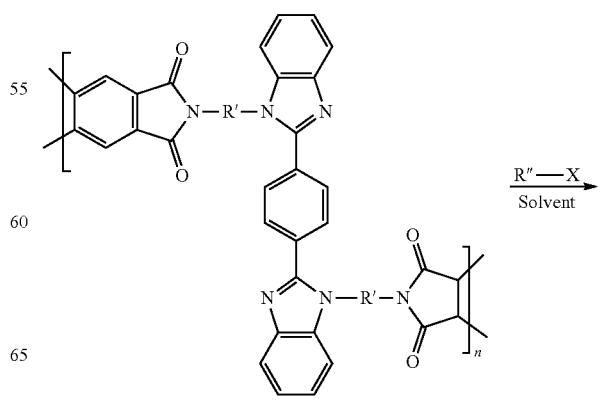

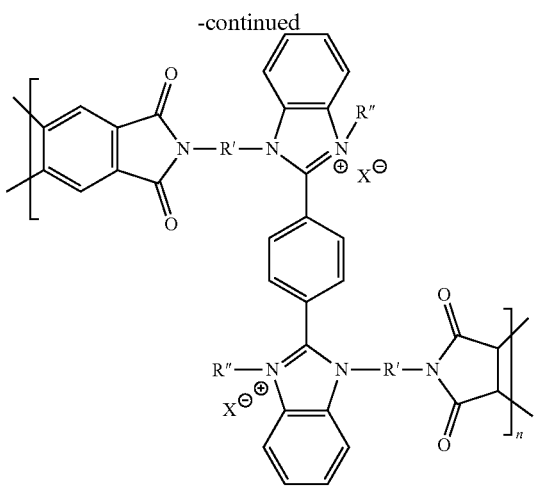

In such aspect, R' can be selected from carboxyl group, hydroxy group, $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, $C_6$-$C_{14}$ aryloxy, $C_3$-$C_{10}$ cycloalkyl, or $C_3$-$C_{10}$ cycloalkenyl, polyester, polysulfone, poly(aryl ether ketone), wherein R' can be optionally substituted with $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, carbonyl, ester, ether, halide, carboxyl, hydroxy, nitro, cyano, silyl, sulfo-oxo, sulfonyl, sulfone, sulfoxide, thiol, or phosphonyl.

In exemplary aspects, R" can be selected from hydrogen, $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, or $C_6$-$C_{14}$ aryloxy, wherein $R^6$, is optionally substituted with $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, carbonyl, ester, ether, halide, carboxyl, hydroxy, nitro, cyano, silyl, sulfo-oxo, sulfonyl, sulfone, sulfoxide, thiol, or phosphonyl.

In these exemplary aspects, n can be an integer from 1 to 100,000. In yet further aspects, n can have integer value in the disclosed range, including exemplary values of 2, 5, 10, 100, 500, 1,000, 5,000, 10,000, 50,000, 80,000, or 90,000. It is understood that n can have any values between any two foregoing values, for example, n can be from 1 to 10 or from 10 to 5,000 or from 50 to 50,000, etc.

Further, in such exemplary aspects, X can be initially selected from halide. Instead of exchanging the anion during the alkylation reaction, the anion can also be optionally exchanged in a separate reaction after the end of the alkylation reaction. For example, the anion could be exchanged for another anion, such as but not limited to chloride, bromide, iodide, nitrate, dicyanamide, acetate, bis(trifluoromethane)sulfonamide, hexafluorophosphate, tetrafluoroborate, sulfate, phosphate, tris(perfluoroalkyl)trifluorophosphatemesylate, aluminum chloride, thiocyanide, mesylate, triflate, or tosylate. Yet, in other aspects, the halide anion can be subsequently exchanged to bistrifilimide ($Tf_2N^-$), triflate ($OTf^-$), or any other anions disclosed herein. In yet further aspects, ionic liquids can be added to the cationic forms of the disclosed polymer to form composites.

Further, the disclosed ionic liquid compositions are materials composed of at least two different ions, each of which can independently and simultaneously introduce a specific characteristic to the composition not easily obtainable with traditional dissolution and formulation techniques. Thus, by providing different ions and ion combinations, one can change the characteristics or properties of the disclosed ionic liquid compositions in a way not seen by simply preparing various crystalline salt forms. Examples of characteristics that can be controlled in the disclosed compositions include, but are not limited to, melting, solubility control, and rate of dissolution. It is this multi-nature/functionality of the disclosed ionic liquid compositions which allows one to fine-tune or design in very specific desired material properties.

It is further understood that the disclosed ionic liquid compositions can include solvent molecules (e.g., water); however, these solvent molecules should not be present in excess in the sense that the disclosed ionic liquid compositions are dissolved in the solvent, forming a solution. That is, the disclosed ionic liquid compositions contain no or minimal amounts of solvent molecules that are free and not bound or associated with the ions present in the ionic liquid composition. Thus, the disclosed ionic liquid compositions can be liquid hydrates or solvates, but not solutions.

Ionic liquids have been of general interest because they are environmentally-friendly alternatives to organic solvents for various chemical processes, e.g., liquid/liquid extractions, catalysis, separations, and electrochemistry. Ionic liquids have also become popular alternative media for chemical synthesis because of their low volatility and low toxicity. See, e.g., Wasserscheid and Keim, *Angew Chem Int Ed Engl*, 2000, 39:3772; and Wasserscheid, "Ionic Liquids in Synthesis," $1^{st}$ Ed., Wiley-VCH, 2002. Further, ionic liquids can reduce costs, disposal requirements, and hazards associated with volatile organic compounds. Other exemplary properties of ionic liquids are high ionic conductivity, non-volatility, non-flammability, high thermal stability, wide temperature for liquid phase, high solvability, and non-coordinating. For a review of ionic liquids, see, for example, Welton, *Chem Rev.* 1999, 99:2071-2083; and Carlin et al., Advances in Nonaqueous Chemistry, Mamantov et al. Eds., VCH Publishing, New York, 1994.

The disclosed ionic liquids can be a liquid at some temperature range or point at or below about 150° C. For example, the disclosed ionic liquids can be a liquid at or below about 150, 149, 148, 147, 146, 145, 144, 143, 142, 141, 140, 139, 138, 137, 136, 135, 134, 133, 132, 131, 130, 129, 128, 127, 126, 125, 124, 123, 122, 121, 120, 119, 118, 117, 116, 115, 114, 113, 112, 111, 110, 109, 108, 107, 106, 105, 104, 103, 102, 101, 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1, 0, −1, −2, −3, −4, −5, −6, −7, −8, −9, −10, −11, −12, −13, −14, −15, −16, −17, −18, −19, −20, −21, −22, −23, −24, −25, −26, −27, −28, −29, or −30° C., where any of the stated values can form an upper or lower endpoint when appropriate. In further examples, the disclosed ionic liquids can be liquid at any point from about −30° C. to about 150° C., from about −20° C. to about 140° C., −10° C. to about 130° C., from about 0° C. to about 120° C., from about 10° C. to about 110° C., from about 20° C. to about 100° C., from about 30° C. to about 90° C., from about 40° C. to about 80° C., from about 50° C. to about 70° C., from about −30° C. to about 50° C., from about −30° C. to about 90° C., from about −30° C. to about 110° C., from about −30° C. to about 130° C., from about −30° C. to about 150° C. to about 30° C. to about 90° C., from about 30° C. to about 110° C., from about 30° C. to about 130° C., from about 30° C. to about 150° C., from about 0° C. to about 100° C., from about 0° C. to about 70° C., from about 0° to about 50° C., and the like.

Further, in some examples, the disclosed ionic liquid compositions can be liquid over a wide range of temperatures, not just a narrow range of, say, 1-2 degrees. For example, the disclosed ionic liquid compositions can be liquids over a range of at least about 4, 5, 6, 7, 8, 9, 10, or more degrees. In another example, the disclosed ionic liquid compositions can be liquid over at least about an 11, 12, 13, 14, 15, 16, 17, 18, 19, 20, or more degree temperature range. Such temperature ranges can begin and/or end at any of the temperature points disclosed in the preceding paragraph.

In many examples disclosed herein, the disclosed ionic liquid compositions are liquid at the temperature at which they will be used or processed (e.g., ambient temperature). In still other examples, the disclosed compositions can be liquid at the temperature at which they are formulated or processed.

It is understood, however, that the disclosed ionic liquid compositions can, though need not, be solubilized, and solutions of the disclosed ionic liquids are contemplated herein. Further, the disclosed ionic liquid compositions can be formulated in an extended or controlled release vehicle, for example, by encapsulating the ionic liquids in microspheres or microcapsules using methods known in the art. Still further, the disclosed ionic liquid compositions can themselves be solvents for other solutes. For example, the disclosed ionic liquids can be used to dissolve a particular nonionic or ionic herbicidal active. These and other formulations of the disclosed ionic liquids are disclosed elsewhere herein.

In some examples, the disclosed ionic liquids are not solutions where ions are dissolved in a solute. In other examples, the disclosed ionic liquid compositions do not contain ionic exchange resins. In still other examples, the disclosed ionic liquids are substantially free of water. By substantially free is meant that water is present at less than about 10, 9, 8, 7, 6, 5, 4, 3, 2, 1, 0.5, 0.25, or 0.1 wt. %, based on the total weight of the composition.

In still further aspects, the compositions formed by the disclosed methods are configured to substantially withstand temperature in a range from about 100° C. to about 600° C., including exemplary values of about 200° C., about 250° C., about 300° C., about 350° C., about 400° C., about 450° C., about 500° C., and about 550° C. In still further aspects, the compositions formed by the disclosed methods substantially withstand temperature in a range from about 100° C. to about 600° C.

In yet further aspects, the compositions formed by the disclosed methods are substantially flame resistant. It is understood that the compositions formed by the disclosed methods are able to withstand fire or give protection from it for a period of time.

Other advantages that are obvious and which are inherent to the invention will be evident to one skilled in the art. It will be understood that certain features and sub-combinations are of utility and may be employed without reference to other features and sub-combinations. This is contemplated by and is within the scope of the claims. Since many possible embodiments may be made of the invention without departing from the scope thereof, it is to be understood that all matter herein set forth or shown in the accompanying drawings is to be interpreted as illustrative and not in a limiting sense.

The invention claimed is:

1. A composition comprising a polymer obtained by polymerizing a mixture comprising a compound having the formula:

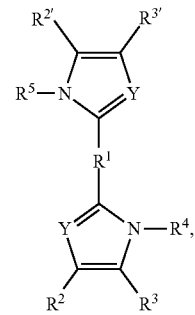

wherein:

$R^1$ is $C_1$-$C_{10}$ alkyl or $C_1$-$C_{10}$ perfluoroalkyl;

Y is N or $N^+$—$R^6$, wherein $R^6$ is $C_1$-$C_{10}$ alkyl, wherein $R^6$ is optionally substituted with $C_6$-$C_{14}$ aryl or $C_1$-$C_{13}$ heteroaryl;

$R^2$, $R^{2'}$, $R^3$, and $R^{3'}$ are, each independent of the other, selected from hydrogen; or wherein $R^2$ and $R^3$ together form a 6 membered ring containing 6 carbon atoms; and/or wherein $R^{2'}$ and $R^{3'}$ together form a 6 membered ring containing 6 carbon atoms;

$R^4$ and $R^5$ are each H or a group having the formula:

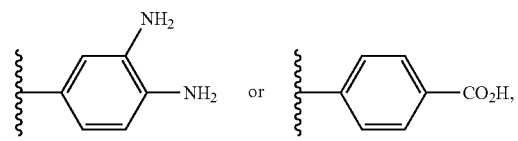 [SMILES: *c1ccc(N)c(N)c1 ; "or" ; *c1ccc(C(=O)O)cc1]

wherein when $R^4$ and $R^5$ are each H, the mixture further comprises a compound of formula X—R'—X, wherein X is a leaving group selected from chlorine, bromine, iodine, mesylate, triflate, and tosylate, and R' is $C_1$-$C_{10}$alkyl or $C_1$-$C_{10}$alkoxy;

when $R^4$ and $R^5$ are each a group having the formula:

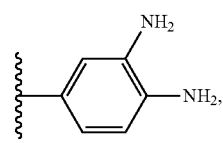 [SMILES: *c1ccc(N)c(N)c1]

the mixture further comprises a compound having the formula:

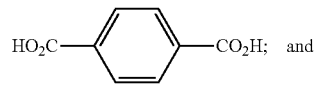

when R⁴ and R⁵ are each a group having the formula:

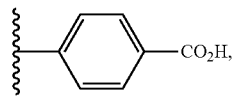 [SMILES: *c1ccc(C(=O)O)cc1]

the mixture further comprises a compound having the formula:

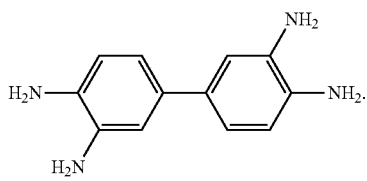

2. The composition according to claim 1, wherein the mixture comprises a compound having the formula:

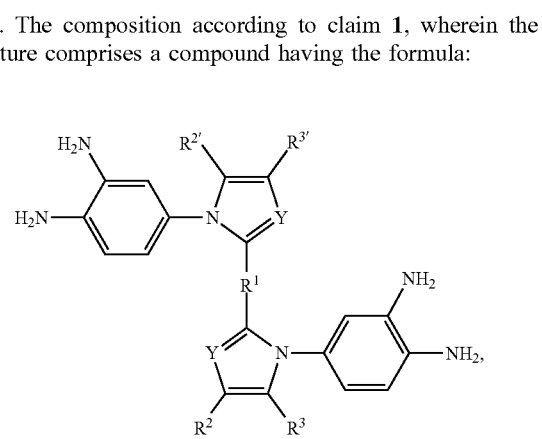

and a compound having the formula:

3. The composition according to claim 1, wherein the mixture comprises a compound having the formula:

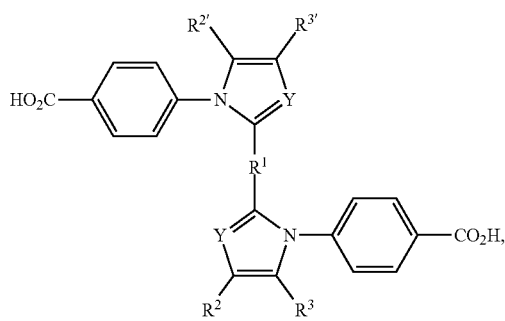

and a compound having the formula:

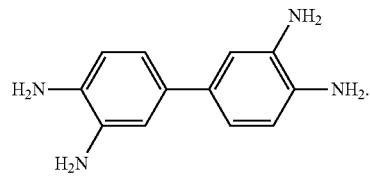 [SMILES: Nc1ccc(-c2ccc(N)c(N)c2)cc1N]

4. The composition according to claim 1, wherein the mixture comprises a compound having the formula:

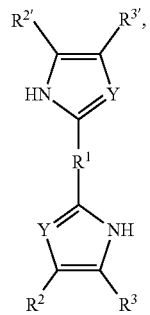

and the mixture further comprises a compound having the formula:

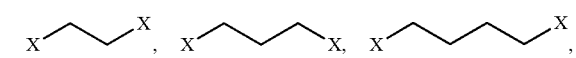

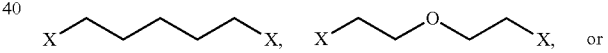

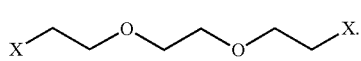

5. The composition according to claim 1, wherein $R^1$ is selected from $CH_2CH_2CH_2CH_2$ or $CF_2CF_2CF_2CF_2$.

6. The composition according to claim 1, wherein Y is N.

7. The composition according to claim 1, wherein Y is $N^+$—$R^6$ and $R^6$ is $C_1$-$C_{10}$ alkyl substituted by an imidazole or imidazolium cation.

8. The composition according to claim 7, wherein $R^6$ has the formula:

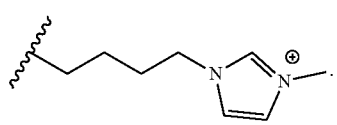 [SMILES: *CCCCn1cc[n+](C)c1]

9. A composition comprising a polymer obtained by polymerizing a mixture comprising a compound having the formula:

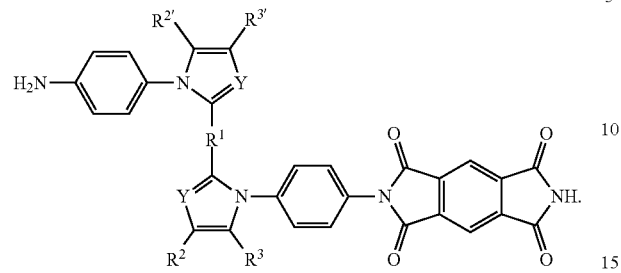

10. The composition according to claim 9, wherein $R^1$ is selected from $CH_2CH_2CH_2CH_2$ or $CF_2CF_2CF_2CF_2$.

11. The composition according to claim 9, wherein Y is N.

12. The composition according to claim 9, wherein Y is $N^+$—$R^6$ and $R^6$ is $C_1$-$C_{10}$ alkyl substituted by an imidazole or imidazolium cation.

13. The composition according to claim 12, wherein $R^6$ has the formula:

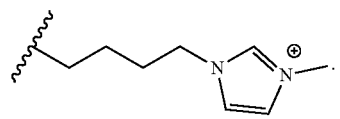 [SMILES: *CCCCn1cc[n+](C)c1]

* * * * *